United States Patent [19]
Naito et al.

[11] Patent Number: 5,602,161
[45] Date of Patent: Feb. 11, 1997

[54] TETRAZOLYLPHENYL PIVALATE DERIVATIVES AND MEDICINAL COMPOSITION CONTAINING THE SAME AS EFFECTIVE COMPONENT

[75] Inventors: Kenji Naito; Ryoki Takahashi; Daisuke Morizono; Mitsuji Agata; Hatsunori Toyofuku; Makoto Maeda, all of Tokyo, Japan

[73] Assignee: Wakamoto Pharmaceutical Co., Ltd., Tokyo, Japan

[21] Appl. No.: 398,786

[22] Filed: Mar. 6, 1995

[30] Foreign Application Priority Data

Mar. 10, 1994 [JP] Japan ..................................... 6-065419

[51] Int. Cl.$^6$ ......................... C07D 257/04; A61K 31/41
[52] U.S. Cl. ........................................... 514/381; 548/253
[58] Field of Search ............................. 548/253; 514/381

[56] References Cited

U.S. PATENT DOCUMENTS

| | | | |
|---|---|---|---|
| 4,683,241 | 7/1987 | Miyano et al. | 514/512 |
| 5,017,610 | 5/1991 | Imaki et al. | 514/546 |
| 5,336,681 | 8/1994 | Imaki et al. | 514/347 |

FOREIGN PATENT DOCUMENTS

| | | |
|---|---|---|
| 0165778 | 12/1985 | European Pat. Off. . |
| 0347168 | 12/1989 | European Pat. Off. . |
| 0539223 | 4/1993 | European Pat. Off. . |

OTHER PUBLICATIONS

Chemical Abstracts, vol. 108, No. 23, AN 204295h, Jun. 6, 1988.
Chemical Abstract, 117:143384y T. Hirano, et al., (Fac. Med., Kyoto Univ., Kyoto, Japan), Med.Sci.Res. 1992, 20(13), 473–4.
Kazuhito Kawabata, et al., "ONO–5046, A Novel Inhibitor of Human Neutrophil Elastase", Biomedical and Biophysical Research Communications, vol. 177, No. 2, 1991, pp. 814–820.
Tetsuya Hirano, et al., "A New Synthetic Elastase Inhibitor, EI–546, Protects Lungs but Not Pancreas in Caerulein–Induced Pancreatitis in the Rat", Med. Sci. Res., 1992, pp. 473–474.
Chemical Abstract, 120:289286b, T. Shintani, et al., (Minase Res. Inst., Ono Pharm. Co., Ltd.) J. Pharm. Biomed. Anal., 1994, 12(3).
Chemical Abstract, 119:181226x K. Imaki, et al., (Ono.Pharm. Co., Ltd.) JP Appl. 91/306,925, Oct. 25, 1991, 16pp.
Chemical Abstract, 117:165785g T. Nozaki, et al., (Sch.Med.,Toho Univ.) Toho Igakkai Zasshi 1993 38(6), 1001–3.
Chemical Abstract, 115:41956c K. Kawabata, et al., (Minase Res.Inst., Ono Pharm. Co., Ltd>) Biochem.Biophys.Res.Commun. 1991, 177(2), 814–20.

*Primary Examiner*—David B. Springer
*Attorney, Agent, or Firm*—Oblon, Spivak, McClelland, Maier & Neustadt, P.C.

[57] ABSTRACT

The tetrazolylphenyl pivalate of the the following general formula or a pharmaceutically acceptable salt thereof:

wherein $R^1$ and $R^2$ each represents a hydrogen atom, a lower alkyl group or other substituents; an elastase-inhibitory composition, a composition for preventing and treating emphysema and a composition for preventing and treating endotoxin-induced lung disorders each comprising the foregoing tetrazolylphenyl pivalate derivative or a non-toxic or acid-addition salt thereof.

21 Claims, No Drawings

TETRAZOLYLPHENYL PIVALATE DERIVATIVES AND MEDICINAL COMPOSITION CONTAINING THE SAME AS EFFECTIVE COMPONENT

BACKGROUND OF THE INVENTION

The present invention relates to a tetrazolylphenyl pivalate derivative represented by the following general formula (1) or a non-toxic or acid-addition salt of the derivative; and a medicinal composition containing the same as an effective component such as an elastase-inhibitory composition, a medicinal composition for preventing and treating emphysema and a medicinal composition for preventing and treating endotoxin-induced lung disorders:

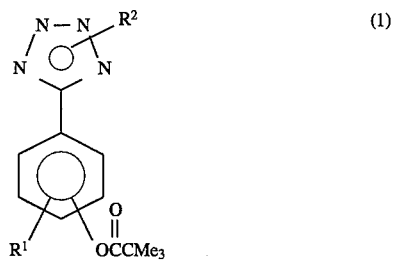

The human leukocyte elastase is a serine protease present in the azurophil granule of the human polymorphonuclear leukocyte and involved in intracellular decomposition of bacteria and foreign proteins after the phagocytosis.

The human leukocyte-derived elastase degrades not only elastin but also various kinds of constitutive proteins including collagen [Biochemical Journal, 1976, 155, p. 265]. The effect of the elastase, in its normal state, is inactivated by the action of $\alpha_1$-protease inhibitor and $\alpha_2$-macroglobulin [Annual Review of Biochemistry, 1983, 52, p. 655].

The inhibitory factors are inactivated or damaged under pathological conditions such as cystic fibrosis [Journal of Respiratory Diseases, 1984, 65, pp. 114–124], emphysema [American Review of Respiratory, 1985, 132, pp. 417–433], acute endogastritis [Bulletin of Toho Medical Society, 1992, 38, No. 6, p. 1001]and chronic arthrorheumatism [Journal of Clinical and Experimental Medicine, 1992, 161, No. 9, p. 597]and this results in an unbalance between the enzyme and the inhibitory factors therefor. This in turn leads to degradation of constitutive proteins such as elastin, collagen and proteoglycan and hence a symptom of histoclasis appears. For this reason, the relation between elastase and these diseases has attracted special interest recently and the elastase-inhibitory agent has been expected as an agent for treating and preventing these diseases.

Under the circumstances discussed above, many attempts have recently been done for studying and developing elastase-inhibitory agents and various elastase-inhibitory agents have been proposed and many patent applications concerning the same were filed.

Elastase-inhibitory agents, in particular, pivalate derivatives are disclosed in, for instance, U.S. Pat. No. 4,683,241, The Journal of Pharmacology and Experimental Therapeutics, 1992, 260, pp. 809–815 and Japanese Un-examined Patent Publication (hereunder referred to as "J.P. KOKAI") No. Hei 3-20253.

SUMMARY OF THE INVENTION

An object of the present invention is to provide a tetrazolylphenyl pivalate derivative or a non-toxic or acid-addition salt thereof having an elastase-inhibitory effect as well as an excellent effect of inhibiting hemorrhage and cell infiltration.

Another object of the present invention is to provide a medicinal composition containing the tetrazolylphenyl pivalate derivative or the foregoing salt thereof as an effective component.

A still another object of the present invention is to provide a medicinal composition, i.e., an elastase-inhibitory composition containing, as an effective component, the tetrazolylphenyl pivalate derivative or the foregoing salt thereof.

A further object of the present invention is to provide medicinal compositions, i.e., a composition for preventing and treating emphysema and a composition for preventing and treating endotoxin-induced lung disorders which comprise the tetrazolylphenyl pivalate derivative or the foregoing salt thereof as effective components.

According to the present invention, there is provided a tetrazolylphenyl pivalate derivative represented by the following general formula (1):

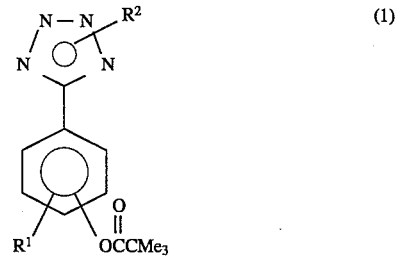

wherein $R^1$ represents a hydrogen atom, a lower alkyl group, a di-lower alkylamino group or a lower alkoxy group; $R^2$ represents (i) a hydrogen atom, (ii) a lower alkyl group, (iii) a group represented by the formula: $—(CH_2)_k —R^3$ (wherein k represents an integer ranging from 1 to 5 and $R^3$ represents an amino group, a carboxyl group, a hydroxyl group, a pyridyl group, a piperidinocarbonyl group, a phenylaminocarbonyl group, a guanidinobenzoyloxy group, a guanidinobenzoylamino group, a lower alkoxycarbonyl group, a di-lower alkylamino group, a tert-butoxycarbonylamino group, or an aralkyloxy group carrying a lower alkoxy group) or (iv) a group represented by the following general formula:

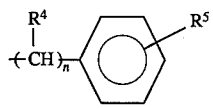

wherein n is an integer ranging from 0 to 4; $R^4$ represents a hydrogen atom, a phenyl group or a group: $—CO—R^{41}$ (wherein $R^{41}$ represents a hydroxyl group, a benzyloxy group or a glycine residue); $R^5$ represents a hydrogen atom, a hydroxyl, carboxyl, nitro, trihalomethyl, lower alkoxy, lower alkyl, lower alkanoyl, carboxy-lower alkoxy, carboxy-lower alkyl, amino-lower alkyl, amino-lower alkoxy, amino-lower alkanoylamino, tert-butoxycarbonyl-lower alkoxy, tert-butoxycarbonylamino-lower alkoxy, (tert-butoxycarbonyl) (lower alkyl)amino, lower alkoxycarbonyl, lower alkoxy group-carrying aralkyloxy, di-lower alkylamino-lower alkyl, di-lower alkylamino-lower alkoxy or lower alkanesulfonamido group, or a group: $—CO—R^{51}$ (wherein $R^{51}$ represents an amino acid residue, an amino acid benzyl ester residue, a benzyloxycarbonylamino-lower alkylamino group or an amino-monolower alkylamino group), or a group represented by the following general formula:

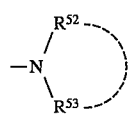

wherein $R^{52}$ and $R^{53}$ may be the same or different and each represents a hydrogen atom or a lower alkyl group or $R^{52}$ and $R^{53}$ may form a heterocyclic ring together with the nitrogen atom to which they are bonded) or non-toxic or acid-addition salts thereof; an elastase-inhibitory composition containing the same as an effective component; a composition for preventing and treating emphysema and a composition for preventing and treating endotoxin-induced lung disorders, each of which comprises the foregoing ester derivative or the salt thereof as an effective component.

The foregoing U.S. Pat. No. 4,683,241, The Journal of Pharmacology and Experimental Therapeutics, 1992, 260, pp. 809–815 and J.P. KOKA No. Hei 3-20253 disclose pivalate derivatives as compounds having an elastase-inhibitory effect. However, the tetrazolylphenyl pivalate derivatives of the present invention are novel compounds having structures different from those disclosed in the foregoing prior arts and there has not been presumed, at all, that these novel compounds exhibit an elastase-inhibitory effect.

It has been reported that the compound, ONO-5046, disclosed in J.P. KOKAI No. Hei 3-20253 shows an effect of inhibiting endotoxin-induced lung disorders [The Course of Medical Science, 1992, 160, No. 4, pp. 257–258], but there is not any report on the hemorrhage-inhibitory effect thereof. Contrary to this, the tetrazolylphenyl pivalate derivatives of the present invention also has an excellent effect of inhibiting hemorrhage and cell infiltration observed when the derivatives are administered to mice suffering from endotoxininduced lung disorders. This fact clearly indicates that the tetrazolylphenyl pivalate derivatives of the present invention are effective for preventing and/or treating adult respiratory distress syndrome (ARDS cases) [Clinical Chest Medicine, 1985, 6, pp. 371–391]; diffuse panlobular bronchitis [Medico, 1990, 21, p.9111]; and pneumonitis [SAISHIN IGAKU, 1992, 47, No. 8, p. 52].

DESCRIPTION OF THE PREFERRED EMBODIMENTS

In the specification, the term "lower" means a group having 1 to 4 carbon atoms in the molecule, unless otherwise specified.

Preferred examples of "lower alkyl group" include linear or branched alkane residues having 1 to 4 carbon atoms such as methyl, ethyl, propyl, isopropyl, butyl, isobutyl and tert-butyl groups.

Preferred examples of "di-lower alkylamino group" are those in which the lower alkyl groups are the same as those listed above in connection with the preferred examples of the "lower alkyl group", with such groups as dimethylamino, diethylamino and dipropylamino groups being more preferred.

Preferred examples of "lower alkoxy group" include linear or branched alkane residues having 1 to 4 carbon atoms such as methoxy, ethoxy, propoxy, butoxy, isobutoxy and tert-butoxy groups, with methoxy and ethoxy groups being more preferred.

Preferred examples of "lower alkoxy group-carrying aralkyloxy group" include those in which the lower alkoxy groups are the same as those listed above in connection with the foregoing preferred "lower alkoxy groups", with methoxybenzyloxy group being more preferred.

Preferred examples of "trihalomethyl group" include trifluoromethyl and trichloromethyl groups.

Preferred examples of "lower alkanoyl group" include linear or branched alkanoyl groups such as formyl, acetyl, propanoyl, butanoyl and 2-methylpropanoyl groups, with such groups as formyl, acetyl and propanoyl being more preferred.

Preferred examples of "carboxy-lower alkoxy group" include those in which the lower alkoxy groups are the same as those listed above in connection with the preferred examples of the foregoing "lower alkoxy groups", with such groups as carboxymethoxy, 2-carboxyethoxy and 3-carboxypropoxy groups being more preferred.

Preferred examples of "carboxy-lower alkyl group" are those in which the lower alkyl groups are the same as those listed above in connection with the preferred examples of the foregoing "lower alkyl groups", with such groups as carboxymethyl, 2-carboxyethyl and 3-carboxypropyl groups being more preferred.

Preferred examples of "amino-lower alkyl group" are those in which the lower alkyl groups are the same as those listed above in connection with the preferred examples of the foregoing "lower alkyl groups", with such groups as aminomethyl, 2-aminoethyl, 3-aminopropyl and 4-aminobutyl groups being more preferred.

Preferred examples of "amino-lower alkoxy group" are those in which the lower alkoxy groups are the same as those listed above in connection with the preferred examples of the foregoing "lower alkoxy groups", with such groups as 2-aminoethoxy, 3-aminopropoxy and 4-aminobutoxy groups being more preferred.

Preferred examples of "amino-lower alkanoylamino group" are those in which the lower alkanoyl groups are the same as those listed above in connection with the preferred examples of the foregoing "lower alkanoyl groups", with such groups as 2-aminoacetylamino, 3-aminopropanoylamino and 4-aminobutanoylamino groups being more preferred.

Preferred examples of "tert-butoxycarbonyl-lower alkoxy group" are those in which the lower alkoxy groups are the same as those listed above in connection with the preferred examples of the foregoing "lower alkoxy groups", with tert-butoxycarbonylmethoxy group being more preferred.

Preferred examples of "tert-butoxycarbonylamino-lower alkoxy group" are those in which the lower alkoxy groups are the same as those listed above in connection with the preferred examples of the foregoing "lower alkoxy groups", with 2-(tert-butoxycarbonylamino)ethoxy group being more preferred.

Preferred examples of "(tert-butoxycarbonyl)(lower alkyl) amino group" are those in which the lower alkyl groups are the same as those listed above in connection with the preferred examples of the foregoing "lower alkyl groups", with such groups as (tert-butoxycarbonyl)(methyl)amino, (tert-butoxycarbonyl)(ethyl)amino and (tert-butoxycarbonyl)(propyl)amino groups being more preferred.

Preferred examples of "lower alkoxycarbonyl group" are those in which the lower alkoxy groups are the same as those listed above in connection with the preferred examples of the foregoing "lower alkoxy groups", with such groups as tert-butoxycarbonyl, butoxycarbonyl, propoxycarbonyl, ethoxycarbonyl and methoxycarbonyl groups being more preferred.

Preferred examples of "di-lower alkylamino-lower alkyl group" are those in which the lower alkyl groups are the same as those listed above in connection with the preferred examples of the foregoing "lower alkyl groups", with such groups as dimethylaminomethyl, 2-dimethylaminoethyl, 3-dimethylaminopropyl, diethylaminomethyl, 2-diethylaminoethyl and 3-diethylamino-propyl groups being more preferred.

Preferred examples of "di-lower alkylamino-lower alkoxy group" are those in which the lower alkyl groups and the lower alkoxy groups are the same as those listed above in connection with the preferred examples of the foregoing "lower alkyl groups" and "lower alkoxy groups" respectively, with such groups as 2-dimethylaminoethoxy, 2-diethylaminoethoxy, 3-dimethylaminopropoxy and 3-diethylaminopropoxy groups being more preferred.

Preferred examples of "lower alkanesulfonamido group" are methanesulfonamido, ethanesulfonamido and propanesulfonamido groups.

Preferred examples of "amino acid residue" are α-amino acids, β-amino acids, γ-amino acids, δ-amino acids and ε-amino acids, with residues of, for instance, glycine, alanine, phenylalanine, serine, threonine, cysteine, methionine, glutamic acid, lysine, proline, valine and ε-caproic acid being more preferred.

Preferred examples of "amino acid benzyl ester residue" are those in which the amino acid residues are the same as those listed above in connection with the preferred examples of the "amino acid residues". More preferred examples thereof include residues of glycine benzyl ester, alanine benzyl ester, phenylalanine benzyl ester, serine benzyl ester, threonine benzyl ester, cysteine benzyl ester, methionine benzyl ester, glutamic acid benzyl ester, lysine benzyl ester, proline benzyl ester and valine benzyl ester.

Preferred examples of "benzyloxycarbonylamino-lower alkylamino group" are those in which the lower alkyl groups are the same as those listed above in connection with the preferred examples of the foregoing "lower alkyl groups", with such groups as 2-(benzyloxycarbonylamino)ethylamino and 3-(benzyloxycarbonylamino)propylamino groups being more preferred.

Preferred examples of "amino-mono-lower alkylamino group" are those in which the lower alkyl groups are the same as those listed above in connection with the preferred examples of the foregoing "lower alkyl groups", with such groups as 2-aminoethylamino, 3-aminopropylamino and 4-aminobutylamino groups being more preferred.

The acid-addition salts of the compound represented by Formula (1) are preferably non-toxic and soluble in water. Examples of appropriate acid-addition salts are salts with inorganic acids such as hydrochlorides, hydrobromides, hydroiodides, sulfates, phosphates and nitrates; and salts with organic acids such as acetates, lactates, tartrates, benzoates, citrates, methanesulfonates, ethanesulfonates, benzenesulfonates, toluenesulfonates, isethionates, glucuronates and gluconates.

The compounds of the present invention represented by Formula (1) can be converted into salts other than the foregoing acid-addition salts by any known method. Such salts are preferably non-toxic and soluble in water. Examples of appropriate salts are alkali metal salts such as sodium and potassium salts; alkaline earth metal salts such as calcium and magnesium salts; ammonium salts; and pharmaceutically acceptable salts with organic amines such as tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, alginine and N-methyl-D-glucamine.

The compounds may be in the form of solvates such as hydrates.

If the compounds of the present invention include asymmetric carbon atoms in the molecules, they may be present in the form of racemic modifications or optical isomers.

The compounds of the invention represented by Formula (1) can be prepared by any one of the following processes. In the following formulae, Z represents a single bond or a lower alkylene group;

$R^{511}$ represents an amino acid benzyl ester residue or an amino acid lower alkyl ester residue;

$R^{512}$ represents an amino acid residue;

$R^{42}$ and $R^{54}$ are groups identical to those defined above in connection with $R^4$ and $R^5$ respectively, provided that at least one of $R^{42}$ and $R^{54}$ represents a group containing a benzyloxy group; $R^{43}$ and $R^{55}$ are groups identical to those defined above in connection with $R^4$ and $R^5$ respectively, provided that at least one of $R^{43}$ and $R^{55}$ represents a group containing a carboxyl group;

$R^{513}$ represents a benzyloxycarbonylamino-lower alkylamino group;

$R^{514}$ represents an amino-lower alkylamino group;

$R^{21}$ has the same meaning as that defined above in connection with $R^2$, but represents a group carrying a lower alkoxybenzyloxy group;

$R^{22}$ has the same meaning as that defined above in connection with $R^2$, but represents a group carrying a hydroxyl group;

$R^6$ represents a lower alkyl group;

$R^{23}$ is a group identical to that defined above in connection with $R^2$, but represents a group carrying a tert-butoxycarbonyl group;

$R^{24}$ is a group identical to that defined above in connection with $R^2$, but represents a group carrying a carboxyl group;

$R^{25}$ is a group identical to that defined above in connection with $R^2$, but represents a group carrying a tert-butoxycarbonylamino group;

$R^{26}$ is a group identical to that defined above in connection with $R^2$, but represents a group carrying an amino group;

Y represents —O— or —NH—;

$R^{521}$ represents a hydrogen atom or a lower alkyl group; and $R^{531}$ represents a lower alkyl group.

Process 1:

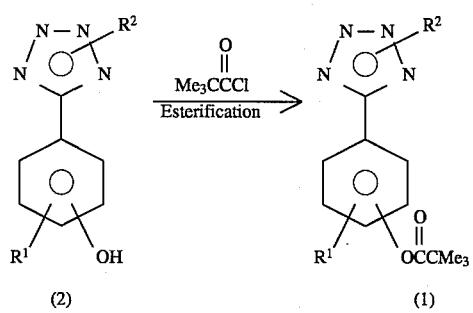

The process 1 is an esterification reaction of the compound of Formula (2). The esterification is carried out by reacting the compound (2) with a pivaloyl halide at room temperature in the presence of a tertiary amine and in an inert organic solvent (for instance, methylene chloride, ethyl acetate, benzene, hexane and/or diethyl ether). A tertiary organic amine and, if necessary, an inorganic base such as a metal bicarbonate may be used as agents for dehydrohalogenation. Examples of such tertiary organic amines usable herein include aliphatic, aromatic or heterocyclic amines such as triethylamine, tributylamine, dimethylaniline and pyridine. Among these, particularly preferred is pyridine since it also serves as a solvent for the components involved in the reaction.

Process 2:

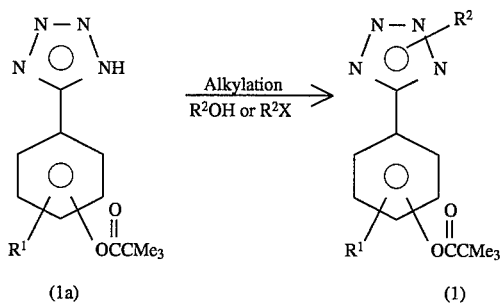

(1a)      (1)

The process 2 is an alkylation reaction of the compound of Formula (1a). The alkylation can be performed using an alkyl halide ($R^2X$) or an alcohol ($R^2OH$). If an alkyl halide is used as an alkylating agent, the alkylation is carried out at a temperature ranging from room temperature to the reflux temperature of a proper inert organic solvent selected from the group consisting of, for instance, dimethylformamide, dimethylsulfoxide, pyridine, methylene chloride, tetrahydrofuran, acetonitrile and chloroform, in the presence of an appropriate base such as sodium hydroxide, sodium hydride, sodium amides, potassium carbonate, potassium bicarbonate, triethylamine or pyridine.

On the other hand, if an alcohol is used as an alkylating agent, the alkylation is carried out at a temperature ranging from 0° C. to the reflux temperature of a proper inert organic solvent selected from the group consisting of, for instance, dimethylformamide, dimethylsulfoxide, methylene chloride, ethyl acetate, tetrahydrofuran, acetonitrile and chloroform and in the presence of a phosphine such as triphenyl phosphine or tributyl phosphine compound and an azo compound such as diethyl azodicarboxylate or diisopropyl azodicarboxylate. The compound of Formula (1a) undergoes the foregoing alkylation reaction at the 1- and 2-positions thereof in a ratio ranging from 1/10 to 1/2.

Process 3:

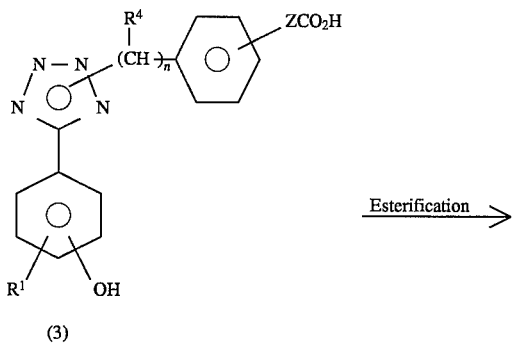

(3)

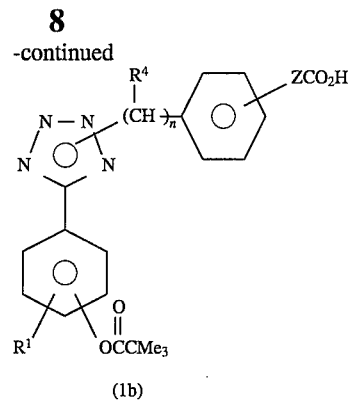

(1b)

The process 3 is an esterification reaction of the compound of Formula (3) which is carried out by reacting the compound (3) with a pivaloyl halide at room temperature in the presence of an inorganic base in a mixed solvent comprising an organic solvent such as acetone, tetrahydrofuran, acetonitrile and/or methanol and water. The inorganic base usable herein may be, for instance, sodium hydroxide and potassium hydroxide.

Process 4:

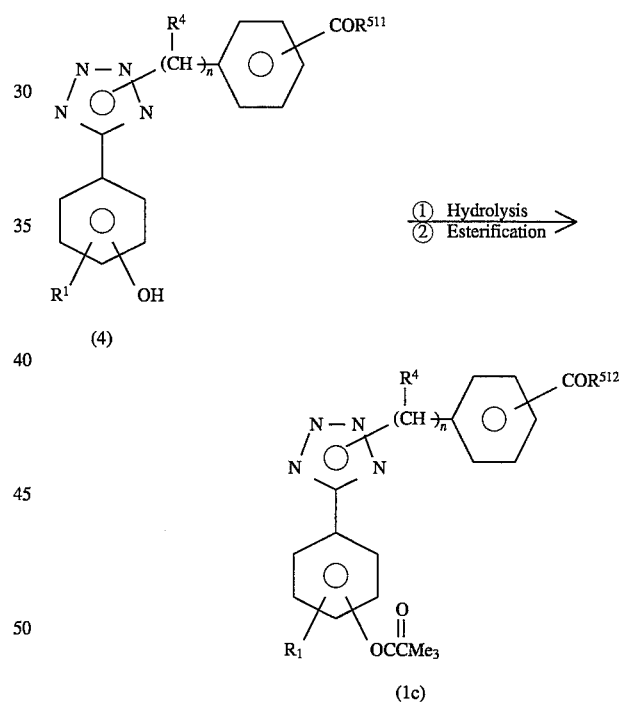

(1c)

The process 4 comprises a hydrolysis reaction and a subsequent esterification reaction of the compound of Formula (4) which are successively carried out. The hydrolysis reaction is performed in a mixed solvent of an organic solvent such as acetone, tetrahydrofuran, acetonitrile and/or methanol with water, in the presence of an inorganic or organic base. Examples of the inorganic bases usable herein are sodium hydroxide, potassium hydroxide, sodium carbonate and potassium carbonate.

The esterification reaction is the same as that used above in the process 3.

Process 5:

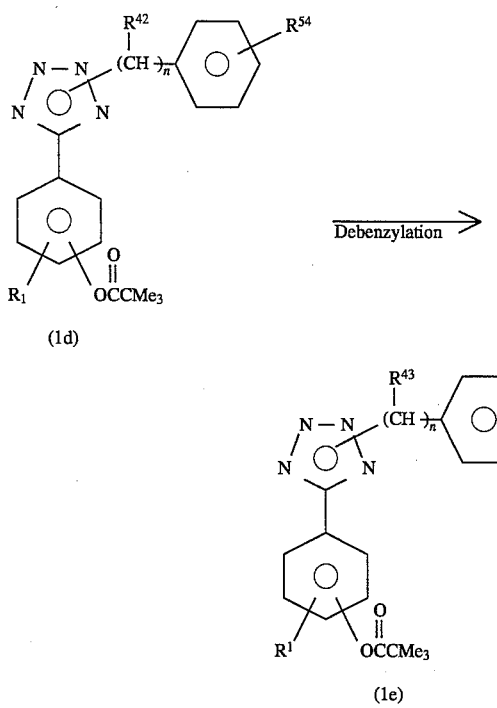

The process 5 is a debenzylation reaction of the compound of Formula (1d) which is carried out at a temperature ranging from 0° C. to 40° C. (preferably room temperature), in a hydrogen gas atmosphere, in the presence of a catalyst such as palladium-carbon and in an inert organic solvent such as acetic acid and/or methanol.

Process 6:

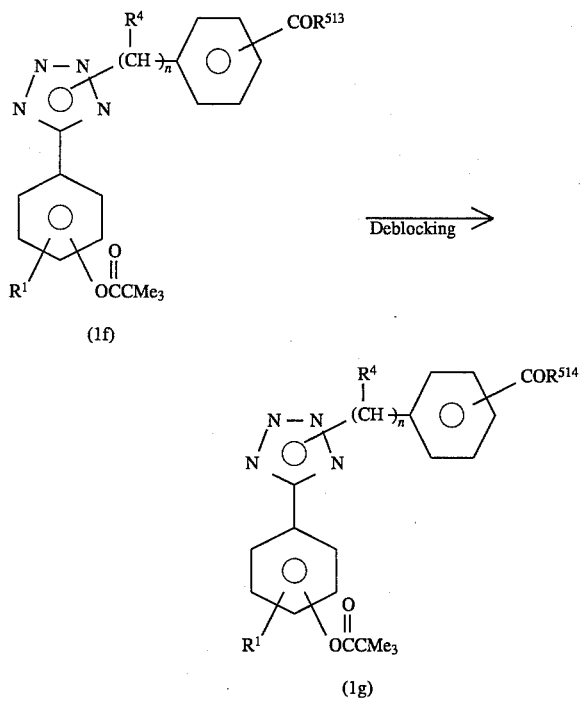

The process 6 is a deblocking reaction of the compound of Formula (1f) through reduction which is carried out at a temperature ranging from 0° to 40° C. (preferably room temperature), in a hydrogen gas atmosphere, in the presence of a catalyst such as palladium-carbon and in an inert organic solvent such as acetic acid and/or methanol.

Process 7:

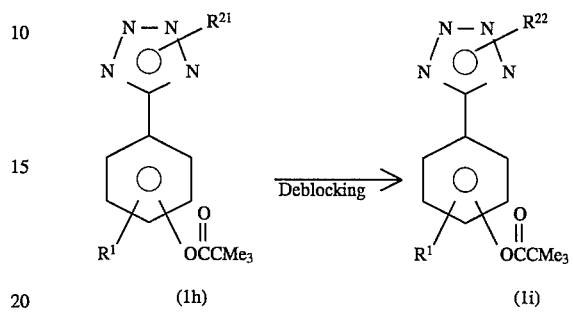

The process 7 is a deblocking reaction of the compound of Formula (1h) through oxidation which is carried out at a temperature ranging from 0° to 40° C. (preferably room temperature), in the presence of an oxidizing agent such as 2,3-dichloro-5,6-dicyano-p-benzoquinone and in a mixed solvent of an inert organic solvent such as methylene chloride and/or ethyl acetate with water.

Process 8:

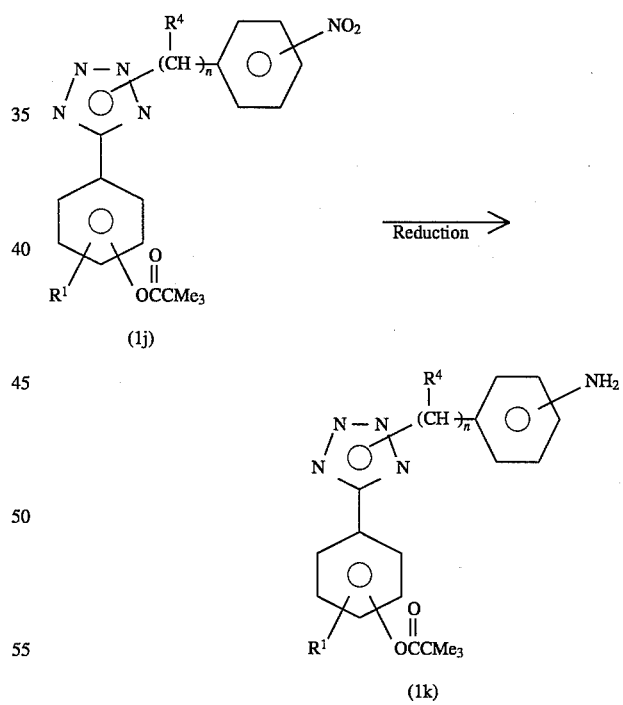

The process 8 is a reduction reaction of the compound of Formula (1j) which is carried out at a temperature ranging from 0° to 40° C. (preferably room temperature), in a hydrogen gas atmosphere, in the presence of a catalyst such as palladium-carbon and in an inert organic solvent such as acetic acid and/or methanol.

Process 9:

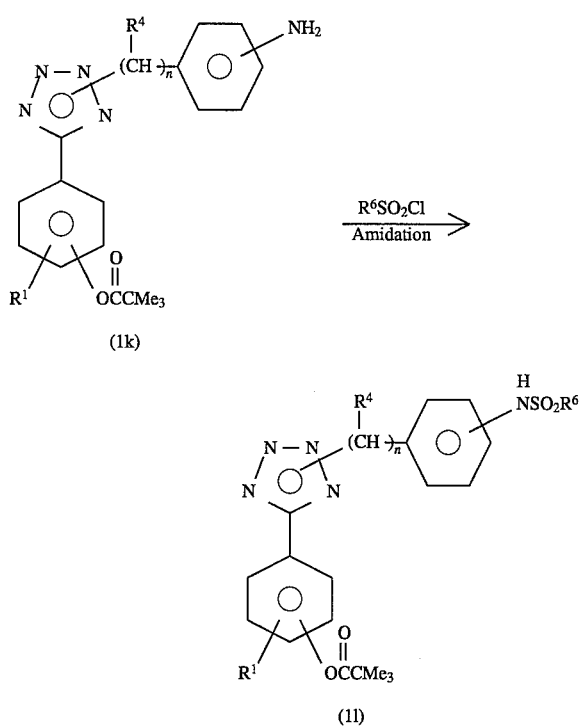

The process 9 is an amidation reaction of the compound of Formula (1k). The amidation is carried out at a temperature ranging from 0° C. to room temperature in an inert organic solvent (such as methylene chloride, ethyl acetate, benzene, hexane and/or diethyl ether) in the presence of a tertiary amine while using a lower alkanesulfonyl chloride. A tertiary organic amine and, if necessary, an inorganic base such as a metal bicarbonate can be used as an agent for dehydrohalogenation. Examples of such tertiary organic amines are aliphatic, aromatic and heterocyclic amines such as triethylamine, tributylamine, dimethylaniline and pyridine. Among these, pyridine is particularly preferred since it also serves as a solvent for the components involved in the reaction.

Process 10:

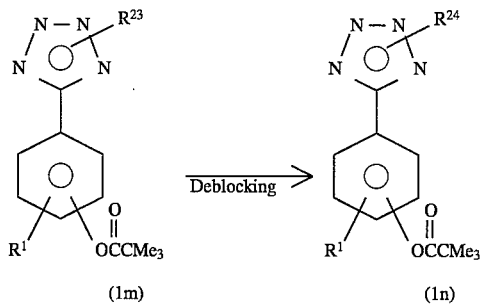

The process 10 is a deblocking reaction of the compound of Formula (1m) and the reaction is carried out at a temperature ranging from 0° to 40° C. (preferably room temperature) in an inert organic solvent such as methylene chloride and/or ethyl acetate while using, for instance, trifluoroacetic acid or hydrochloric acid. The use of trifluoroacetic acid is particularly preferred since it also serves as a solvent for the components involved in the reaction.

Process 11:

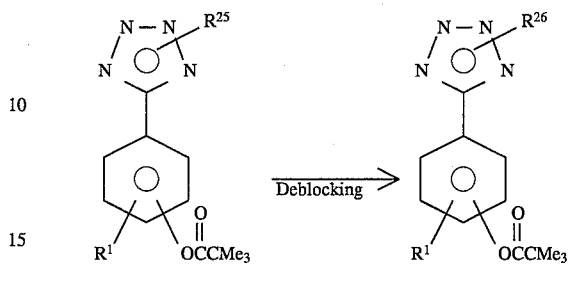

The process 11 is a deblocking reaction of the compound of Formula (1o). The reaction is carried out at a temperature ranging from 0° C. to 40° C. (preferably room temperature) in an inert organic solvent such as methylene chloride and/or ethyl acetate while using, for instance, trifluoroacetic acid or hydrochloric acid. The use of trifluoroacetic acid is particularly preferred since it also serves as a solvent for the components involved in the reaction.

Process 12:

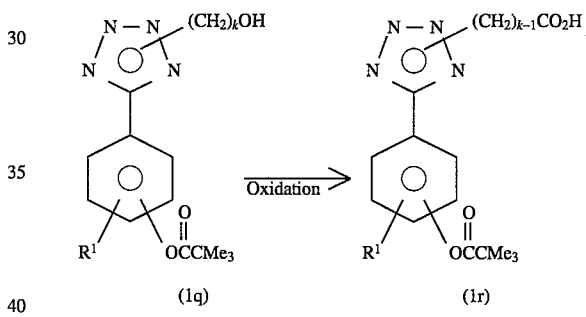

The process 12 is an oxidation reaction of the compound of Formula (1q). The oxidation reaction is carried out at a temperature ranging from 0° C. to 40° C. (preferably room temperature) in a mixed solvent of carbon tetrachloride, acetonitrile and water, while using ruthenium chloride in the presence of sodium periodate.

Process 13:

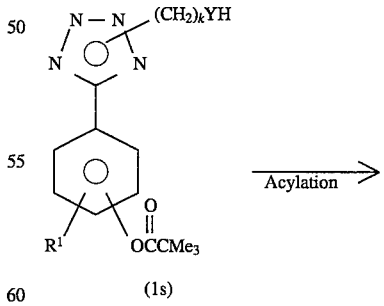

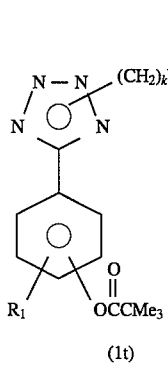

(1t)

Process 15:

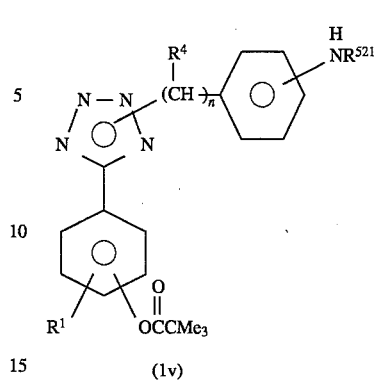

The process 13 is an acylation reaction of the compound of Formula (1s). The acylation is carried out at a temperature ranging from 0° C. to room temperature in an inert organic solvent such as methylene chloride, ethyl acetate, benzene, hexane and/or diethyl ether in the presence of a tertiary amine while using a corresponding acid chloride. A tertiary orgnic amine and, if necessary, an inorganic base such as a metal bicarbonate can be used as agents for dehydrohalogenation. Examples of such tertiary organic amines are aliphatic, aromatic and heterocyclic amines such as triethylamine, tributylamine, dimethylaniline and pyridine. Among these, pyridine is particularly preferred since it also serves as a solvent for the components involved in the reaction.

Process 14:

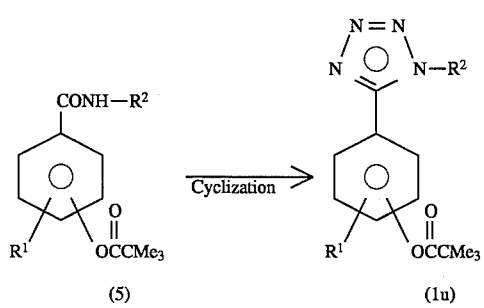

The process 14 is a tetrazole ring-forming reaction. The cyclization reaction is carried out by reacting the compound of Formula (5) with a chlorinating agent such as phosphorus pentachloride at a temperature ranging from 0° C. to room temperature in an inert organic solvent such as methylene chloride and/or benzene to give an imidoyl chloride and then reacting the resulting imidoyl chloride with sodium azide at a temperature ranging from 0° C. to room temperature in dimethylformamide or water.

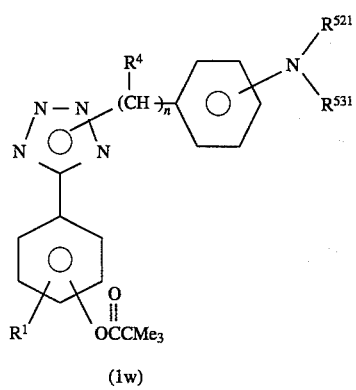

(1w)

The process 15 is an alkylating reaction of the compound of Formula (1v) which is alkylated with an alkyl halide. The alkylation is carried out at a temperature ranging from room temperature to the reflux temperature of an appropriate inert organic solvent such as dimethylformamide, dimethylsulfoxide, methylene chloride, tetrahydrofuran, acetonitrile and/or chloroform and preferably in the presence of an appropriate base such as sodium hydroxide, potassium hydroxide, sodium azide, sodium carbonate, potassium carbonate, triethylamine and/or pyridine.

The compounds of Formulae (2), (3), (4) and (5) used in the foregoing processes can be prepared by any combination of known reactions, for instance, according to the following reaction scheme. In the following reaction scheme, $R^7$ and $R^8$ each represents a lower alkyl group and other substituents are the same as those defined above.

Reaction Scheme

1. 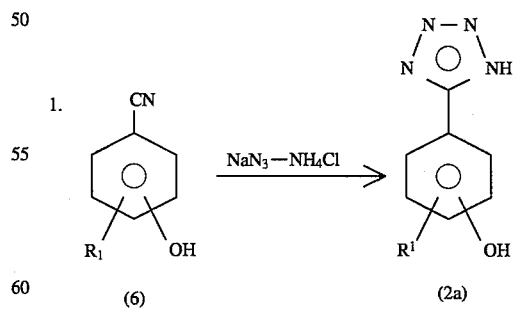

2. 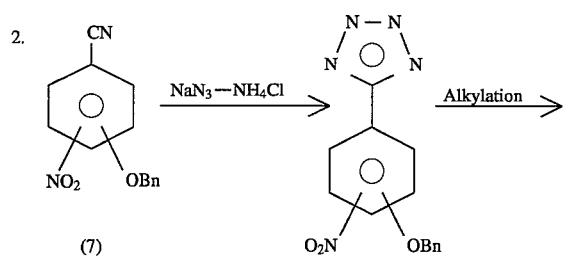
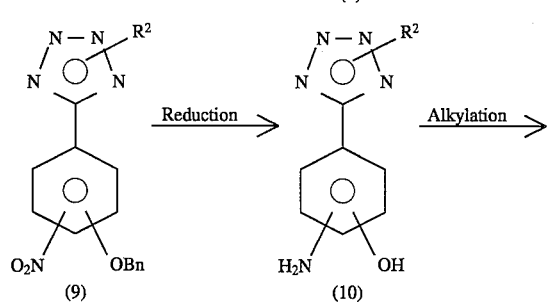
3. 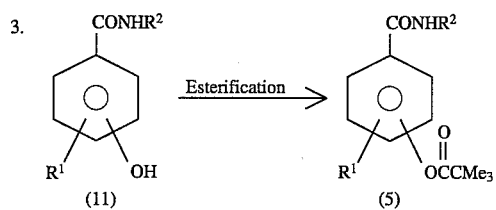
4. 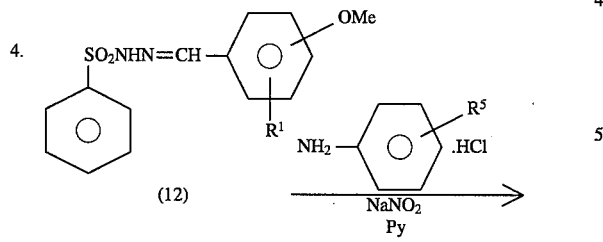
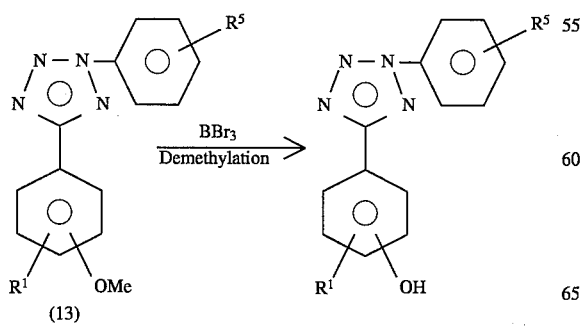
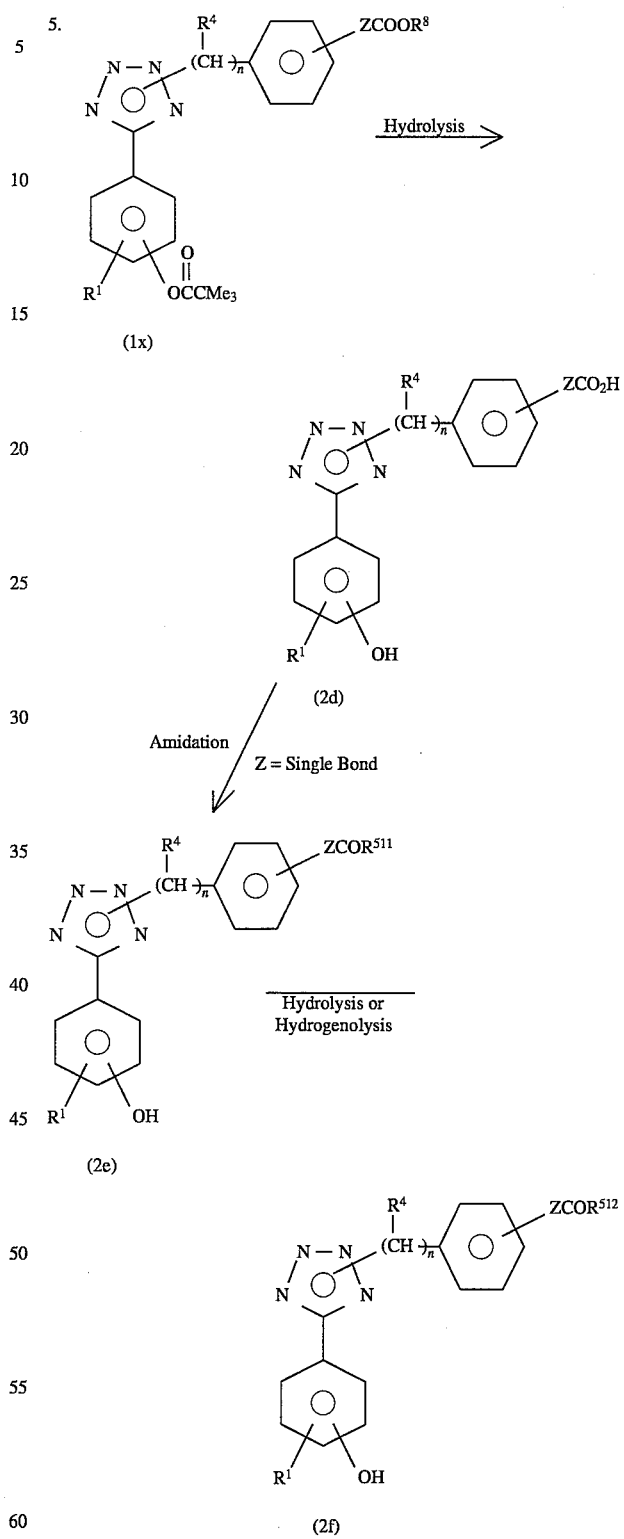
All of the reactions included in the foregoing reaction scheme are carried out by any known methods. In each reaction appearing in this specification, the reaction product can be purified by currently used purification means such as distillation performed at ordinary pressure or reduced pressure, high performance liquid chromatography, thin layer chromatography or column chromatography which makes use of silica gel or magnesium silicate, washing and/or recrystallization. The purification may be carried out after each reaction or after completion of a series of or several successive reactions.

Moreover, all of the starting materials represented by Formulas (6), (7), (11) and (12) used in the method of the present invention are known per se or can easily be prepared by any known methods.

REFERENCE EXAMPLES AND WORKING EXAMPLES

The present invention will be explained in detail by the following reference examples and working examples to which the invention is not limited.

Reference example 1

2-(1H-Tetrazol-5-yl)phenol

2-Cyanophenol (1.19 g), ammonium chloride (0.695 g), and sodium azide (0.845 g) were added to dimethylformamide (5 ml). The mixture was heated with stirring at 120° C. for 3 h. After cooling, it was poured into ice water and acidified with dilute hydrochloric acid. The resulting crystals were collected by filtration and dried to give the title compound.

yield 1.34 g (83.7%)

m.p.: 228° C.

I.R. $v_{KBr}$ cm$^{-1}$: 3400–2800,1620,1490,1470,1360

N.M.R.(DMSO-d$_6$) δ: 7.00(1H,dd,J=7.8,7.3),7.06(1H,d,J=7.3), 7.40(1H,t,J=7.3),8.00(1H,d,J=7.8)

Example 1

2-(1H-Tetrazol-5-yl)phenyl pivalate 2-(1H-Tetrazol-5-yl)phenol (4.86 g) was dissolved in pyridine (20 ml), and pivaloyl chloride (7.2 g) was added to the solution at room temperature. After being stirred for 15 h, the mixture was poured into ice water and acidified with dilute hydrochloric acid. The resulting crystals were collected by filtration and dried to give the title compound.

yield 4.73 g (64%)

m.p.: 82°–85° C.

I.R. $v_{KBr}$ cm$^{-1}$: 1770,1490,1210,1120

N.M.R.(CDCl$_3$) δ: 1.38(9H,s),7.20(1H,d,J=8.0),7.34(1H,t,J=8.0), 7.55(1H,t,J=8.0),7.94(1H,d,J=8.0)

The following compounds were obtained from corresponding starting materials by the same procedures as reference example 1 and example 1.

Example 2

3-(1H-Tetrazol-5-yl)phenyl pivalate yield 68% m.p.: 237°–238° C.

I.R. $v_{KBr}$ cm$^{-1}$: 1750,1515,1465,1120

N.M.R.(DMSO-d$_6$) δ: 1.34(9H,s),7.36(1H,d,J=8.0), 7.66(1H,t,J=8.0), 7.78(1H,s),7.94(1H,d,J=8.0)

Example 3

4-(1H-Tetrazol-5-yl)phenyl pivalate yield 95% m.p.: 136°–138° C.

I.R. $v_{KBr}$ cm$^{-1}$: 1748,1110

N.M.R.(DMSO-d$_6$) δ: 1.41(9H,s),7.43(2H,d,J=8.5), 8.18(2H,d,J=8.5),

Example 4

2-Methyl-4-(1H-tetrazol-5-yl)phenyl pivalate yield 84% m.p.: 165° C. (dec.)

I.R. $v_{KBr}$ cm$^{-1}$: 3000–2400,1750,1495,1230,1130

N.M.R.(CDCl$_3$) δ: 1.43(9H,s),2.22(3H,s),7.09(1H,d,J=8.3), 7.75(1H,dd,J=8.3,2.0),7.87(1H,d,J=2.0)

Example 5

2-Methoxy-4-(1H-tetrazol-5-yl)phenyl pivalate yield 70% m.p.: 198°–200° C.

I.R. $v_{KBr}$ cm$^{-1}$: 3000–2400,1760,1505,1265,1120

N.M.R.(CDCl$_3$) δ: 1.43(9H,s),3.77(3H,s),7.07(1H,d,J=8.3), 7.36(1H,dd,J=8.3,1.7),7.48(1H,d,J=1.7)

Reference example 2

4-[2-(4-Isopropylphenyl)tetrazol-5-yl]phenol

4-Isopropylaniline (1.35 g) was added to a mixed solution of 50% ethanol (16 ml) and concentrated hydrochloric acid (2.6 ml). To the mixture was added a solution of sodium nitrite (0.69 g) in water (4 ml) over 10 min below 5° C. and stirring was continued for 10 min. To a solution of 4-methoxybenzaldehyde phenylsulfonylhydrazone (2.9 g) in pyridine (60 ml) was added dropwise the above solution of diazonium salt during 20 min at −10° C.—−15° C., and stirring was continued for 30 min at −10° C. and for 30 min at room temperature. The mixture was poured into ice water and extracted with ethyl acetate. The extract was washed succesively with 4 N hydrochloric acid, water, aqueous sodium carbonate,and water, dried, and evaporated to dryness. The residue was purified by column chromatography on silica gel with benzene-hexane (1/2-2/1) as an eluate to give 2-(4-isopropylphenyl)-5-(4-methoxyphenyl)tetrazole (1.6 g,54%). To a solution of 2-(4- isopropylphenyl)-5-(4-methoxyphenyl)tetrazole (1.3 g) in dichloromethane (10 ml) was added dropwise boron tribromide (10 ml,2.6M solution in dichloromethane) at −10° C. Stirring was continued for 1 h at −10° C. and for 1 h at room temperature. To the mixture was added water (20 ml), and the mixture was extracted with chloroform. The extract was washed with water, dried and evaporated to dryness. The residue was recrystallized from benzene to give 1.1 g (72%) of the title compound.

m.p.: 158°–160° C.

I.R. $v_{KBr}$ cm$^{-1}$: 1615,1440,1280,840

N.M.R.(CDCl$_3$) δ: 1.31(6H,d,J=6.8),3.01(1H,septet,J=6.8), 5.77(1H,s),7.00(2H,d,J=8.8),7.41(2H,d,J=8.8), 8.08(2H,d,J=8.8),8.13(2H,d,J=8.8)

Example 6

4-[2-(4-Isopropylphenyl)tetrazol-5-yl)phenyl pivalate

Triethylamine (0.167 g) and 4-dimethylaminopyridine (0.02 g) were added to a solution of 4-[2-(4-isopropylphenyl)tetrazol-5-yl]phenol (0.42 g), obtained in the reference example 2, in dichloromethane (5 ml), and pivaloyl chloride (0.199 g) was added to the solution under ice cooling. Stirring was continued for 1 h at the same temperature. The mixture was washed with water, dried and evaporated to dryness. The residue was recrystallized from ethyl acetate-hexane to give 0.3 g (55%) of the title compound.

m.p.: 122°–125° C.

I.R. $v_{KBr}$ cm$^{-1}$: 1760,1520,1470,1210,1120

N.M.R.(CDCl$_3$) δ: 1.31(6H,d,J=6.8),1.39(9H,s), 3.01(1H, septet,J=6.8),7.23(2H,d,J=8.8), 7.41(2H,d,J=8.8),8.09(2H, d,J=8.8), 8.27(2H,d,J=8.8)

Reference example 3

5-(4-Benzyloxy-3-nitrophenyl)-1H-tetrazole

The title compound was prepared by treating with the same procedure as reference example 1 with use of 4-benzyloxy-3-nitrobenzonitrile as a starting material.

yield : 58% m.p.: 178°–180° C.

I.R. $v_{KBr}$ cm$^{-1}$: 3100–2400,1630,1530,1350,1300

N.M.R.(CDCl$_3$) δ: 5.42(2H,s),7.30–7.53(5H,m),7.72(1H, d,J=8.8), 8.30(1H,dd,J=8.8,2.0),8.55(1H,d,J=2.2)

Reference example 4

5-(4-Benzyloxy-3-nitrophenyl)-2-[4-(dimethylamino)-benzyl]tetrazole

A solution of diethyl azodicarboxylate (522 mg) in tetrahydrofuran (3 ml) was added dropwise to a solution of 5-(4-benzyloxy-3-nitrophenyl)-1H-tetrazole (594 mg), obtained in reference example 3, triphenylphosphine (786 mg) and 4-dimethylaminobenzyl alcohol (378 mg) in tetrahydrofuran (5 ml) for 10 min under ice cooling, and stirring was continued for 15 h at room temperature. The tetrahydrofuran was evaporated. The residue was purified by column chromatography on silica gel with ethyl acetate-hexane (1/3) as an eluate to give 320 mg (37%) of the title compound as crystals.

m.p.: 118°–120° C.

I.R. $v_{KBr}$ cm$^{-1}$: 1610,1550,1520,1350,1290

N.M.R.(CDCl$_3$) δ: 2.94(6H,s),5.29(2H,s),5.67(2H,s), 6.68(2H,d,J=8.8),7.15–7.50(8H,m), 8.25(1H,dd,J=8.8,2.2), 8.58(1H,d,J=2.2)

Reference example 5

2-Dimethylamino-4-[2-[4-(dimethylamino)benzyl]-tetrazol-5-yl]phenol

A solution of 5-(4-benzyloxy-3-nitrophenyl)-2-[4-(dimethylamino) benzyl]tetrazole (200 mg), obtained in reference example 4, in a mixed solution of methanol (10 ml) and ethyl acetate (2 ml) was hydrogenated over 5% palladium carbon (50 mg) under a hydrogen atmosphere at room temperature. After the reaction was completed, the catalyst was filtered off, and the filtrate was evaporated to dryness. The residue was dissolved in methanol (10 ml), and aqueous 37% formaldehyde (37 mg) was added to the solution. After being stirred for 5 min, sodium cyanoborohydride (7 mg) was added to it, and stirring was continued for 1 h at room temperature. This treatment was repeated once again. The solvent was evaporated, and the residue was extracted with ethyl acetate. The extract was washed with water, dried, and evaporated to dryness. The residue was purified by column chromatography on silica gel with chloroform-methanol (50/1) as an eluate to give 93 mg (57%) of the title compound.

N.M.R.(CDCl$_3$) δ: 2.69(6H,s),2.94(6H,s),5.66(2H,s), 6.68(2H,d,J=8.5),7.00(1H,d,J=8.3), 7.32(2H,d,J=8.5), 7.82(1H,dd,J=8.3,2.0), 7.94(1H,d,J=2.0)

Example 7

2-Dimethylamino-4-[2-[4-(dimethylamino)benzyl]-tetrazol-5-yl]phenyl pivalate The title compound was prepared by treating with the same procedure as example 6 with use of 2-dimethylamino-4-[2-[4-(dimethylamino) benzyl]tetrazol-5-yl]phenol, obtained in reference example 5, as a starting material.

yield 70% m.p.: 73°–74° C.

I.R. $v_{KBr}$ cm$^{-1}$: 1755,1105

N.M.R.(CDCl$_3$) δ: 1.39(9H,s),2.78(6H,s),2.94(6H,s), 5.68(2H,s), 6.68(2H,d,J=8.5),7.00(1H,d,J=8.3), 7.31(2H,d, J=8.5),7.70(1H,dd,J=8.3,2.0), 7.78(1H,d,J=2.0)

Reference example 6

Methyl 4-[5-(3-dimethylamino-4-hydroxyphenyl)tetrazol-2-ylmethyl]benzoate

The title compound was obtained from a corresponding starting material by treating with the same procedure as reference example 4 and reference example 5.

N.M.R.(CDCl$_3$) δ: 2.70(6H,s),3.91(3H,s),5.83(2H,s), 7.02(1H,d,J=8.3),7.44(2H,d,J=8.3), 7.83(1H,dd,J=8.3, 2.0)7.95(1H,d,J=2.0), 8.05(2H,d,J=8.3)

Example 8

4-[5-(3-Dimethylamino-4-pivaloyloxyphenyl)tetrazol-2-ylmethyl]benzoic acid

To a solution of aqueous 10% sodium hydroxide (0.67 ml) in methanol (5 ml) was added methyl 4-[5-(3-dimethylamino-4-hydroxyphenyl)tetrazol-2-ylmethyl]benzoate (296 mg) obtained in reference example 6. The mixture was heated at 50° C. for 1 h, and the solvent was evaporated. To the residue were added acetone (10 ml) and H$_2$O (10 ml), and pivaloyl chloride (150 mg) was added dropwise to it under ice cooling. The mixture was stirred at the same temperature for 1 h, acidified with aqueous citric acid, and extracted with ethyl acetate. The extract was dried and evaporated to dryness. The residue was purified by column chromatography on silica gel with chloroform-methanol (100/4–5) as an eluate to give 46 mg (12%) of the title compound.

m.p.: 177°–178° C.

I.R. $v_{KBr}$ cm$^{-1}$: 1750,1115

N.M.R.(CDCl$_3$) δ: 1.39(9H,s),2.79(6H,s),5.86(2H,s), 7.02(1H,d,J=8.3), 7.46(2H,d,J=8.5),7.73(1H,d,J=8.3), 7.79(1H,s), 8.09(2H,d,J=8.5)

Example 9

4-(2-Benzyltetrazol-5-yl)phenyl pivalate

A mixture of 4-(1H-tetrazol-5-yl)phenyl pivalate (1.23 g) obtained in example 3, potassium carbonate (0.69 g), and benzyl chloride (0.63 g) in dimethylformamide (10 ml) was stirred at room temperature for 15 h. The mixture was poured into ice water and extracted with ethyl acetate. The extract was washed with water, dried, and evaporated to dryness. The residue was recrystallized from ethyl acetate-hexane to give 1.07 g of the title compound.

m.p.: 131°–134° C.

I.R. $\nu_{KBr}$ cm$^{-1}$: 1780,1150

N.M.R.(CDCl$_3$) δ: 1.36(9H,s),5.79(2H,s),7.17(2H,d,J= 6.8), 7.35–7.45(5H,m), 8.15(2H,d,J=6.8)

The following compounds were obtained from corresponding starting materials by the same procedures as example 9.

Example 10

4-[2-(t-Butoxycarbonylmethyl)tetrazol-5-yl]phenyl pivalate yield 47% m.p.: 152°–154° C.

I.R. $\nu_{KBr}$ cm$^{-1}$: 1745,1110

N.M.R.(CDCl$_3$) δ: 1.37(9H,s),1.48(9H,s),5.34(2H,s), 7.20(2H,d,J=8.8), 8.18(2H,d,J=8.8)

Example 11

4-[2-(N-Phenylcarbamoylmethyl)tetrazol-5-yl]phenyl pivalate yield 51.5% m.p.: 183°–186° C.

I.R. $\nu_{KBr}$ cm$^{-1}$: 3375,1750,1735,1708,1685,1465,1120

N.M.R.(CDCl$_3$) δ: 1.39(9H,s),5.39(2H,s),7.14(1H,t,J= 7.3), 7.22(2H,d,J=8.8),7.32(2H,t,J=7.3), 7.47(2H,d,J=7.3), 7.95(1H,s),8.18(2H,d,J=8.8)

Example 12

4-[2-(Piperidinocarbonylmethyl)tetrazol-5-yl]phenyl pivalate yield 52% m.p.: 188°–191° C.

I.R. $\nu_{KBr}$ cm$^{-1}$: 1740,1660,1470,1115

N.M.R.(CDCl$_3$) δ: 1.37(9H, s),1.55–1.75(6H,m), 3.46(2H,t,J=5.1), 3.59(2H,t,J=5.1),5.52(2H,s),7.19(2H,d,J= 8.5), 8.18(2H,d,J=8.5)

Example 13

4-[2-(4-Methoxybenzyl)tetrazol-5-yl]phenyl pivalate yield 34.5% m.p.: 118°–120° C.

I.R. $\nu_{KBr}$ cm$^{-1}$: 1740,1470,1120

N.M.R.(CDCl$_3$) δ: 1.36(9H,s),3.79(3H,s),5.72(2H,s), 6.90(2H,d,J=8.8), 7.17(2H,J=8.8),7.38(2H,d,J=8.8), 8.14(2H,d,J=8.8)

Example 14

4-[2-(2-Phenylethyl)tetrazol-5-yl]phenyl pivalate yield 65% m.p.: 95°–98° C.

I.R. $\nu_{KBr}$ cm$^{-1}$: 1760,1460,1110

N.M.R.(CDCl$_3$) δ: 1.37(9H,s),3.37(2H,t,J=7.8),4.87(2H, t,J=7.8), 7.20(4H,d,J=8.5),7.23–7.34(3H,m),8.16(2H,d,J= 8.5)

Example 15

4-[2-(Benzyloxymethyl)tetrazol-5-yl]phenyl pivalate yield 74% m.p.: 74°–76° C.

I.R. $\nu_{KBr}$ cm$^{-1}$: 1750,1470,1120,1105

N.M.R.(CDCl$_3$) δ: 1.38(9H,s),4.71(2H,s),5.96(2H,s), 7.22(2H,d,J=8.5), 7.35(5H,s),8.21(2H,d,J=8.5)

Example 16

4-[2-[4-(Dimethylamino)benzyl]tetrazol-5-yl]phenyl pivalate yield 18.7% m.p.: 157°–160° C.

I.R. $\nu_{KBr}$ cm$^{-1}$: 1750,1620,1120

N.M.R.(CDCl$_3$) δ: 1.36(9H,s),2.94(6H,s),5.68(2H,s), 6.69(2H,d,J=8.5), 7.15(2H,d,J=8.5),7.33(2H,d,J=8.5), 8.14(2H,d,J=8.5)

Example 17

4-[2-(4-Trifluoromethylbenzyl)tetrazol-5-yl]phenyl pivalate yield 59.4% m.p.: 126°–129° C.

I.R. $\nu_{KBr}$ cm$^{-1}$: 1750,1460,1330,1120

N.M.R.(CDCl$_3$) δ: 1.37(9H,s),5.86(2H,s),7.18(2H,d,J= 8.5), 7.52(2H,d,J=8.1),7.66(2H,d,J=8.1), 8.15(2H,d,J=8.5)

Example 18

4-[2-[4-(4-Methoxybenzyloxy)benzyl]tetrazol-5-yl]-phenyl pivalate yield 63.6% m.p.: 144°–146° C.

I.R. $\nu_{KBr}$ cm$^{-1}$: 1760,1520,1465,1120

N.M.R.(CDCl$_3$) δ: 1.36(9H,s),3.80(3H,s),4.97(2H,s), 5.72(2H,s), 6.90(2H,d,J=8.5),6.96(2H,d,J=8.5),7.17(2H,d, J=8.5), 7.33(2H,d,J=8.5),7.37(2H,d,J=8.5),8.14(2H,d,J=8.5)

Example 19

4-[2-(4-Isopropylbenzyl)tetrazol-5-yl]phenyl pivalate yield 10.5% m.p.: 110°–113° C.

I.R. $\nu_{KBr}$ cm$^{-1}$: 1750,1470,1210,1130

N.M.R.(CDCl$_3$) δ: 1.23(6H,d,J=7.1),1.36(9H,s),2.90(1H,septet,J=7.1), 5.75(2H,s),7.16(2H,d,J=8.3),7.24(2H,d,J=8.3), 7.35(2H,d,J=8.3),8.15(2H,d,J=8.3)

Example 20

4-[2-[3-(4-Methoxyphenyl)propyl]tetrazol-5-yl]phenyl pivalate yield 57.5% m.p.: 78°–80° C.

I.R. $\nu_{KBr}$ cm$^{-1}$: 1745,1460,1250,1120

N.M.R.(CDCl$_3$) δ: 1.37(9H,s),2.36(2H,quintet,7.0), 2.65(2H,t,J=7.0), 3.79(3H,s),4.63(2H,t,J=7.0),6.85(2H,d,J=8.5), 7.12(2H,d,J=8.8),7.19(2H,d,J=8.8),8.16(2H,d,J=8.5)

Example 21

4-[2-[4-(4-Methoxyphenyl)butyl]tetrazol-5-yl]phenyl pivalate yield 41% m.p.: 70°–73° C.

I.R. $\nu_{KBr}$ cm$^{-1}$: 1750,1515,1465,1120

N.M.R.(CDCl$_3$) δ: 1.37(9H,s),1.61–1.72(2H,m),2.07(2H,quintet,J=7.5), 2.62(2H,t,J=7.5),3.77(3H,s),4.64(2H,t,J=7.1), 6.81(2H,d,J=8.5),7.07(2H,d,J=8.5),7.18(2H,d,J=8.8), 8.16(2H,d,J=8.8)

Example 22

2-[2-[4-(4-Methoxybenzyloxy)butyl]tetrazol-5-yl]phenyl pivalate yield 51% oil

I.R. $\nu_{neat}$ cm$^{-1}$: 1755,1615,1510

N.M.R.(CDCl$_3$) δ: 1.39(9H,s),1.63–1.68(2H,m),2.15(2H,quintet,J=7.5), 3.48(2H,t,J=6.1),3.79(3H,s),4.42(2H,s), 4.64(2H,t,J=7.5),6.87(2H,d,J=8.8),7.13(1H,d,J=8.0), 7.24(2H,d,J=8.8),7.36(1H,t,J=8.0),7.48(1H,t,J=8.0), 8.19(1H,d,J=8.0)

Example 23

3-[2-[4-(4-Methoxybenzyloxy)butyl]tetrazol-5-yl]phenyl pivalate yield 63% oil

I.R. $\nu_{neat}$ cm$^{-1}$: 1760,1620,1520,1470

N.M.R.(CDCl$_3$) δ: 1.38(9H,s),1.62–1.72(2H,m),2.6(2H,quintet,J=7.1), 3.49(2H,t,J=6.1),3.79(3H,s),4.43(2H,s) 4.67(2H,t,J=7.1),6.87(2H,d,J=8.8),7.16(1H,d,J=8.0), 7.25(2H,d,J=8.8),7.49(1H,t,J=8.0),7.84(1H,brs), 8.00(1H,d,J=8.0)

Example 24

4-[2-(2-Methoxycarbonylbenzyl)tetrazol-5-yl]phenyl pivalate yield 63% m.p.: 100°–103° C.

I.R. $\nu_{KBr}$ cm$^{-1}$: 1760,1730,1470,1280,1120

N.M.R.(CDCl$_3$) δ: 1.37(9H,s),3.95(3H,s),6.32(2H,s), 6.96(1H,d,J=7.5), 7.18(2H,d,J=8.5),7.40–7.53(2H,m), 8.07(1H,dd,J=7.5,1.8),8.16(2H,d,J=8.5)

Example 25

4-[2-(4-Nitrobenzyl)tetrazol-5-yl]phenyl pivalate yield 70% m.p.: 143°–145° C.

I.R. $\nu_{KBr}$ cm$^{-1}$: 1750,1530,1470,1350,1120

N.M.R.(CDCl$_3$) δ: 1.37(9H,s),5.91(2H,s),7.18(2H,d,J=8.8),

Example 26

4-[2-(3-Nitrobenzyl)tetrazol-5-yl]phenyl pivalate yield 73.5% m.p.: 124°–126° C.

I.R. $\nu_{KBr}$ cm$^{-1}$: 1740,1540,1460,1360,1200,1120

N.M.R.(CDCl$_3$) δ: 1.37(9H,s),5.91(2H,s),7.19(2H,d,J=8.5), 7.60(1H,t,J=7.9),7.74(1H,d,J=7.9),8.15(2H,d,J=8.5), 8.25(1H,d,J=7.9),8.34(1H,s)

Example 27

4-[2-(2-Nitrobenzyl)tetrazol-5-yl]phenyl pivalate yield 61.6% m.p.: 134°–135° C.

I.R. $\nu_{KBr}$ cm$^{-1}$: 1740,1540,1470,1210,1120

N.M.R.(CDCl$_3$) δ: 1.37(9H,s),6.30(2H,s),6.93(1H,d,J=7.3), 7.20(2H,d,J=8.5),7.53–7.64(2H,m),8.15–8.23(3H,m)

Example 28

4-[2-(Diphenylmethyl)tetrazol-5-yl]phenyl pivalate yield 12% m.p.: 145°–147° C.

I.R. $\nu_{KBr}$ cm$^{-1}$: 1750,1465,1210,1120

N.M.R.(CDCl$_3$) δ: 1.36(9H,s),7.30–7.40(13H,m), 8.17(2H,d,J=8.8)

Example 29

4-[2-(4-Acetylbenzyl)tetrazol-5-yl]phenyl pivalate yield 57% m.p.: 130°–132° C.

I.R. $\nu_{KBr}$ cm$^{-1}$: 1762,1680,1470,1205,1120

N.M.R.(CDCl$_3$) δ: 1.37(9H,s),2.59(3H,s),5.86(2H,s), 7.18(2H,d,J=8.8), 7.49(2H,d,J=8.3),7.98(2H,d,J=8.3), 8.14(2H,d,J=8.8)

Example 30 t-Butyl 2-[5-(4-pivaloyloxyphenyl)tetrazol-2-ylmethyl]-phenoxyacetate yield 83.9% m.p.: 84°–86° C.

I.R. $\nu_{KBr}$ cm$^{-1}$: 1750,1730,1460,1200,1160,1120

N.M.R.(CDCl$_3$) δ: 1.37(9H,s),1.46(9H,s),4.59(2H,s), 5.94(2H,s), 6.80(1H,d,J=8.3),6.98(1H,t,J=7.6),7.16(3H,m), 7.31(1H,td,J=8.3,1.5),8.16(2H,d,J=8.6)

Example 31 t-Butyl 3-[5-(4-pivaloyloxyphenyl)tetrazol-2-ylmethyl]-phenoxyacetate yield 80.9% m.p.: 118°–119° C.

I.R. $\nu_{KBr}$ cm$^{-1}$: 1760,1740,1460,1160,1120

N.M.R.(CDCl$_3$) δ: 1.37(9H,s),1.46(9H,s),4.50(2H,s), 5.75(2H,s), 6.88(1H,dd,J=7.8,2.2),6.94(1H,brs),7.03(1H,d,J=7.8), 7.17(2H,d,J=8.8),7.30(1H,t,J=7.8),8.15(2H,d,J=8.8)

Example 32 t-Butyl 4-[5-(4-pivaloyloxyphenyl)tetrazol-2-ylmethyl]-phenoxyacetate yield 89.4% m.p.: 107°–109° C.

I.R. $\nu_{KBr}$ cm$^{-1}$: 1750,1515,1460,1210,1150,1120

N.M.R.(CDCl$_3$) δ: 1.37(9H,s),1.47(9H,s),4.50(2H,s), 5.73(2H,s), 6.89(2H,d,J=8.6),7.17(2H,d,J=8.6),7.37(2H,d,J=8.6), 8.17(2H,d,J=8.6)

Example 33

4-[2-[4-[2-(t-Butoxycarbonylamino)ethoxy]benzyl]-tetrazol-5-yl]phenyl pivalate m.p.: 130° C.

I.R. $\nu_{KBr}$ cm$^{-1}$: 3475,1740,1705,1515,1250,1170,1120

N.M.R.(CDCl$_3$) δ: 1.36(9H, s),1.43(9H,s),3.45–3.55(2H, m), 4.00(2H,t,J=5.2),4.94(1H,brs),5.72(2H,s), 6.89(2H,d,J=8.8),7.16(2H,d,J=8.5) 7.37(2H,d,J=8.8),8.14(2H,d,J=8.5)

Example 34

4-[2-[2-[2-(t-Butoxycarbonylamino)ethoxy]benzyl]-tetrazol-5-yl ]phenyl pivalate oil I.R. $\nu_{KBr}$ cm$^{-1}$: 1750,1710,1460,1165,1110

N.M.R.(CDCl$_3$) δ: 1.36(9H,s),1.42(9H,s),3.50–3.60(2H, m), 4.04(2H,t,J=4.9),5.47(1H,brs),5.83(2H,s), 6.87(1H,d,J=8.0),6.98(1H,t,J=7.0) 7.16(2H,d,J=8.8),7.30–7.40(2H,m), 8.14(2H,d,J=8.8)

Example 35

4-[2-(4-Pyridylmethyl)tetrazol-5-yl]phenyl pivalate yield 44.5% m.p.: 98°–102° C.

I.R. $\nu_{KBr}$ cm$^{-1}$: 1750,1465,1205,1120

N.M.R.(CDCl$_3$) δ: 1.37(9H,s),5.82(2H,s),7.18(2H,d,J=8.8), 7.25(2H,d,J=6.1),8.16(2H,d,J=8.8),8.64(2H,d,J=6.1)

Example 36

4-[2-(1,1-Dimethylethyl)tetrazol-5-yl]phenyl pivalate yield 59.5% m.p.: 102°–103° C.

I.R. $\nu_{KBr}$ cm$^{-1}$: 1750,1460,1200,1105

N.M.R.(CDCl$_3$) δ: 1.38(9H,s),1.80(9H,s),7.18(2H,d,J=8.8), 8.20(2H,d,J=8.8)

Example 37

4-[2-(2-Methylpropyl)tetrazol-5-yl]phenyl pivalate yield 89.9% m.p.: 92°–93° C.

I.R. $\nu_{KBr}$ cm$^{-1}$: 1750,1460,1200,1115

N.M.R.(CDCl$_3$) δ: 1.01(6H,d,J=6.8),1.38(9H,s),2.44(1H, sept,J=6.8), 4.46(2H,d,J=6.8),7.12(2H,d,J=8.9),8.17(2H,d,J=8.9)

Example 38

4-[2-(2-Dimethylaminoethyl)tetrazol-5-yl]phenyl pivalate Hydrochloride yield 35.6% m.p.: 228°–229° C.

I.R. $\nu_{KBr}$ cm$^{-1}$: 1750,1460,1200,1110

N.M.R.(CDCl$_3$) δ: 1.33(9H,s),2.87(6H,s),3.81(2H,t,J=6.4), 5.27(2H,t,J=6.4),7.33(2H,d,J=8.7),8.14(2H,d,J=8.7)

Example 39

4-[2-[4-(N-t-Butoxycarbonyl-N-methylamino)benzyl]-tetrazol-5-yl]phenyl pivalate A solution of diethyl azodicarboxylate (1.74 g) in tetrahydrofuran (5 ml) was added dropwise to a solution of 4-(1H-tetrazol-5-yl)phenyl pivalate (1.23 g), obtained in example 3, t-butyl N-methyl-N-(4-hydroxymethylphenyl) carbamate (1.11 g) and triphenylphosphine (2.62 g) in tetrahydrofuran (10 ml) for 30 min under ice cooling. Stirring was continued for 15 h at room temperature. After evaporating in vacuo, the residue was purified by column chromatography on silica gel to give the title compound. The first elute with ethyl acetate-hexane (3/7) was evaporated and crystallization from hexane gave 0.92 g (40.8 of the title compound.

m.p.: 87°–90° C.

I.R. $\nu_{KBr}$ cm$^{-1}$: 2975,1750,1700,1465,1370,1120

N.M.R.(CDCl$_3$) δ: 1.37(9H,s),1.44(9H,s),3.23(3H,s), 5.76(2H,s), 7.17(2H,d,J=8.8),7.26(2H,d,J=8.3),7.37(2H,d,J=8.3), 8.15(2H,d,J=8.8)

Example 40

4-[1-[4-(N-t-Butoxycarbonyl-N-methylamino)benzyl]-tetrazol-5-yl]phenyl pivalate In the chromatography on silica gel in example 39, the second elute with ethyl acetate-hexane (3/7) was evaporated to give 0.55 g (24%) of the title compound as an oil.

I.R. $\nu_{neat}$ cm$^{-1}$: 2975,1750,1705,1480,1370,1110

N.M.R.(CDCl$_3$) δ: 1.37(9H,s),1.44(9H,s),3.24(3H,s), 5.58(2H,s), 7.13(2H,d,J=8.8),7.23(2H,d,J=8.8),7.25(2H,d,J=8.8), 7.62(2H,d,J=8.8)

Example 41

4-[2-[2-(4-Methoxybenzyloxy)ethyl]tetrazol-5-yl]phenyl pivalate

To a solution of 4-(1H-tetrazol-5-yl)phenyl pivalate (1.476 g), obtained in example 3, 2-(4-methoxybenzyloxy)ethanol (1.41 g), and triphenylphosphine (2.67 g) in tetrahydrofuran (10 ml) was added dropwise a solution of diethyl azodicarboxylate (1.77g) in tetrahydrofuran (5 ml) for 30 min under ice cooling. Stirring was continued for 15 h at room temperature. After evaporating in vacuo, the residue was purified by column chromatography on silica gel with ethyl acetate-hexane (1/4) to give 2.1 g (85%) of the title compound as an oil.

I.R. $\nu_{neat}$ cm$^{-1}$: 1750,1460,1110

N.M.R.(CDCl$_3$) δ: 1.38(9H,s),3.74(3H,s),4.00(2H,t,J=5.6),4.46(2H,s), 4.81(2H,t,J=5.4),6.81(2H,d,J=8.8), 7.14(2H,d,J=8.8), 7.19(2H,d,J=8.8),8.16(2H,d,J=8.8)

The following compounds were obtained from corresponding starting materials by the same procedures as example 41.

Example 42

4-[2-[4-(4-Methoxybenzyloxy)butyl]tetrazol-5-yl]phenyl pivalate yield 84% oil

I.R. $\nu_{neat}$ cm$^{-1}$: 1750,1460,1250,1120

N.M.R.(CDCl$_3$) δ: 1.37(9H,s),1.60–1.75(2H,m),2.16(2H, quintet,J=7.1), 3.50(2H,t,J=6.1),3.79(3H,s),4.42(2H,s), 4.66(2H,t,J=7.1),6.87(2H,d,J=8.5),7.19(2H,d,J=8.5), 7.25(2H,d,J=8.5),8.16(2H,d,J=8.5)

Example 43

4-[2-[5-(4-Methoxybenzyloxy)pentyl]tetrazol-5-yl]-phenyl pivalate yield 86% oil

I.R. $\nu_{neat}$ cm$^{-1}$: 1750,1510,1110

N.M.R.(CDCl$_3$) δ: 1.37(9H,s),1.42–1.53(2H,m), 1.60–1.73(2H,m), 2.05–2.14(2H,m),3.44(2H,t,J=6.1), 3.79(3H,s), 4.41(2H,s),4.63(2H,t,J=7.1),6.86(2H,d,J=8.8), 7.18(2H,d,J=8.8),7.24(2H,d,J=8.8),8.16(2H,d,J=8.8)

Example 44

4-[2-[2-(4-Methoxyphenyl)ethyl]tetrazol-5-yl]phenyl pivalate yield 35% m.p.: 86°–89° C.

I.R. $\nu_{KBr}$ cm$^{-1}$: 1750,1515,1460,1200,1120

N.M.R.(CDCl$_3$) δ: 1.37(9H,s),3.31(2H,t,J=7.5),3.77(3H, s), 4.82(2H,t,J=7.5),6.83(2H,d,J=8.5),7.10(2H,d,J=8.5), 7.19(2H,d,J=8.5),8.16(2H,d,J=8.5)

Example 45

4-[2-[2-(t-Butoxycarbonylamino)ethyl]tetrazol-5-yl]-phenyl pivalate yield 44.6% m.p.: 133°–135° C.

I.R. $\nu_{KBr}$ cm$^{-1}$: 3375,1750,1690,1525,1110

N.M.R.(CDCl$_3$) δ: 1.38(9H,s),1.43(9H,s),3.70–3.85(2H, m), 4.77(2H,t,J=7.7),4.90(1H,brs),7.19(2H,d,J=8.5), 8.16(2H,d,J=8.5)

Example 46

4-[2-[4-(2-Dimethylaminoethoxy)benzyl]tetrazol-5-yl]-phenyl pivalate Hydrochloride yield 14.6% m.p.: 188°–190° C.

I.R. $\nu_{KBr}$ cm$^{-1}$: 2975,1755,1470,1120

N.M.R.(DMSO-d$_6$) δ: 1.32(9H,s),2.81(6H,s),3.48(2H,t, J=5.0), 4.35(2H,t,J=5.0),5.93(2H,s), 7.03(2H,d,J=8.5), 7.29(2H,d,J=8.3), 7.43(2H,d,J=8.5),8.08(2H,d,J=8.3), 10.36(1H,s)

Example 47

4-[2-[4-(Dimethylaminomethyl)benzyl]tetrazol-5-yl]-phenyl pivalate yield 15% m.p.: 122°–125° C.

I.R. $\nu_{KBr}$ cm$^{-1}$: 1755,1470,1125

N.M.R.(CDCl$_3$) δ: 1.36(9H,s),2.22(6H,s),3.41(2H,s), 5.78(2H,s), 7.17(2H,d,J=8.8),7.32(2H,d,J=8.1),7.38(2H,d, J=8.1), 8.15(2H,d,J=8.8)

Example 48

4-[2-[4-(Dimethylamino)benzyl]tetrazol-5-yl]-2-methoxyphenyl pivalate yield 53.1% m.p.: 98°–100° C.

I.R. $\nu_{KBr}$ cm$^{-1}$: 3000–2800,1760,1530,1480,1270,1110

N.M.R.(CDCl$_3$) δ: 1.38(9H,s),2.94(6H,s),3.89(3H,s), 5.68(2H,s), 6.69(2H,d,J=8.8),7.08(1H,d,J=8.6),7.32(2H,d, J=8.8), 7.72(1H,d,J=8.6),7.73(1H,s)

Example 49

4-[2-[4-(Dimethylamino)benzyl]tetrazol-5-yl]-2-methylphenyl pivalate yield 53.1% m.p.: 139°–141° C.

I.R. $\nu_{KBr}$ cm$^{-1}$: 1750,1530,1460,1125

N.M.R.(CDCl$_3$) δ: 1.39(9H,s),2.23(3H,s),2.95(6H,s), 5.68(2H,s), 6.69(2H,d,J=8.8),7.06(1H,d,J=8.3),7.33(2H,d, J=8.8), 7.96(1H,d,J=8.3),8.01(1H,s)

Example 50

4-[2-(4-Pyrrolidinobenzyl)tetrazol-5-yl]phenyl pivalate yield 12.5% m.p.: 151°–153° C.

I.R. $\nu_{KBr}$ cm$^{-1}$: 1750,1530,1460,1120

N.M.R.(CDCl$_3$) δ: 1.37(9H,s),1.96–2.00(4H,m), 3.24–3.29(4H,m), 5.67(2H,s),6.53(2H,d,J=8.8),7.15(2H,d, J=8.8), 7.32(2H,d,J=8.8),8.13(2H,d,J=8.8)

Example 51

4-[2-[α-(Benzyloxycarbonyl)benzyl]tetrazol-5-yl]-phenyl pivalate yield 63% m.p.: 91°–93° C.

I.R. $v_{KBr}$ cm$^{-1}$: 3450,1750,1460,1200,1110

N.M.R. (CDCl$_3$) δ: 1.37(9H,s),5.26(2H,ABq,J=12.0), 6.72(1H,s), 7.17(2H,d,J=8.7),7.20–7.58(10H,m),8.15(2H,d, J=8.7)

Reference example 7

2-[5-(4-Hydroxyphenyl)tetrazol-5-ylmethyl]benzoic acid

A solution of 4-[2-(2-methoxycarbonylbenzyl)tetrazol-5-yl]phenyl pivalate (1 g), obtained in example 24, and aqueous 1N sodium hydroxide (5.58 ml) in methanol (10 ml) was heated with stirring at 50° C. for 30 min. Ater cooling, the mixture was acidified with dilute hydrochloric acid and extracted with ethyl acetate. The extract was dried and evaporated to dryness. The residue was recrystallized from ethyl acetate-hexane to give 720 mg (96%) of the title compound.

I.R. $v_{KBr}$ cm$^{-1}$: 3300–2600,1690,1615,1460,1280,1260

N.M.R.(CDCl$_3$) δ: 6.34(2H,s),6.84(1H,d,J=7.3),6.92(2H,d,J=8.8), 7.35–7.50(2H,m),7.96(2H,d,J=8.8), 8.11(1H,dd,J=7.5,1.7),9.30(1H,brs)

Example 52

2-[5-(4-Pivaloyloxyphenyl)tetrazol-2-ylmethyl]benzoic acid

A solutin of pivaloyl chloride (77 mg) in acetone (0.5 ml) was added dropwise to a solution of 2-[5-(4-hydroxyphenyl)tetrazol-2-ylmethyl]benzoic acid (190 mg), obtained in reference example 7, and aqueous 1N sodium hydroxide (1.28 ml) in acetone (2 ml) under ice cooling. Stirring was continued for 1 h at the same temperature. After the acetone was evaporated in vacuo, the residue was acidified with dilute hydrochloric acid and extracted with ethyl acetate. The extract was dried and evaporated to dryness. The residue was purified by column chromatography on silica gel with chloroform-methanol (100/5) as an eluate and crystallization from hexane gave 110 mg (45 of the title compound.

m.p.: 138°–140° C.

I.R. $v_{KBr}$ cm$^{-1}$: 1750,1700,1470,1120

N.M.R.(DMSO-d$_6$) δ: 1.32(9H,s),6.35(2H,s),7.19(1H,d,J=7.3), 7.29(2H,d,J=8.5),7.47–7.57(2H,m),7.98(1H,d,J=7.5), 8.08(2H,d,J=8.5)

The following compounds were obtained from corresponding starting materials by the same procedures as reference example 7 and example 52.

Example 53

4-[5-(4-Pivaloyloxyphenyl)tetrazol-2-ylmethyl]-phenylacetic acid yield 31.6% m.p.: 155°–156° C.

I.R. $v_{KBr}$ cm$^{-1}$: 3000–2800,1750,1705,1470,1210,1115

N.M.R.(CDCl$_3$) δ: 1.36(9H,s),3.55(2H,s),5.73(2H,s), 7.15(2H,d,J=8.8), 7.23(2H,d,J=8.4),7.32(2H,d,J=8.4), 8.12(2H,d,J=8.8)

Example 54

4-[5-(4-Pivaloyloxyphenyl)tetrazol-2-ylmethyl]benzoic acid yield 17.4% m.p.: 192°–193° C.

I.R. $v_{KBr}$ cm$^{-1}$: 3000–2900,1755,1700,1465,1205,1120

N.M.R.(CDCl$_3$) δ: 1.38(9H,s),5.89(2H,s),7.19(2H,d,J=8.4), 7.47(2H,d,J=8.4),8.07(2H,d,J=6.4),8.15(2H,d,J=6.4)

Example 55

4-[5-(3-Methyl-4-pivaloyloxyphenyl)tetrazol-2-ylmethyl]benzoic acid yield 45.6% m.p.: 190°–191° C.

I.R. $v_{KBr}$ cm$^{-1}$: 1750,1700,1120

N.M.R.(CDCl$_3$) δ: 1.39(9H,s),2.23(3H,s),5.87(2H,s), 7.09(1H,d,J=8.0), 7.48(2H,d,J=8.0),7.98(1H,d,J=8.0), 8.02(1H,s), 8.11(2H,d,J=8.0)

Example 56

4-[5-(3-Methoxy-4-pivaloyloxyphenyl)tetrazol-2-ylmethyl]benzoic acid yield 28% m.p.: 214°–215° C.

I.R. $v_{KBr}$ cm$^{-1}$: 3000–2800,1760,1480,1420,1270,1120

N.M.R.(DMSO-d$_6$) δ: 1.33(9H,s),3.86(3H,s),6.02(2H,s), 7.19(1H,d,J=9.5), 7.40(2H,d,J=8.1),7.67(1H,d,J=9.5), 7.69(1H,s), 7.98(2H,d,J=8.1)

Reference example 8

Ethyl N-[4-[5-(4-hydroxyphenyl)tetrazol-2-ylmethyl]-benzoyl]-L-alaninate

4-[5-(4-Hydroxyphenyl)tetrazol-2-ylmethyl]benzoic acid (296 mg), which was obtained from a corresponding starting material by the same procedures as reference example 7, alanine ethyl ester hydrochloride (153.5 mg),l-hydroxybenzotriazole (153 mg), and triethylamine (101 mg) were dissolved in a mixed solution of dichloromethane (5 ml) and dimethylformamide (2 ml). To it was added dicyclohexylcarbodiimide (206 mg) under ice cooling, and stirring was continued for 5 h at room temperature. The dichloromethane was evaporated. Ethyl acetate was added to the mixture, and the resulting precipitate was filtered off. The ethyl acetate layer was washed succesively with an aqueous sodium hydrogencarbonate solution, 1N hydrochloric acid and water, dried, and evaporated to dryness. The residue was purified by column chromatography on silica gel with ethyl acetate-hexane (1/1) as an elute to give 240 mg (60%) of the title compound.

N.M.R.(CDCl$_3$) δ: 1.27(3H,t,J=7.1),1.49(3H,d,J=7.3), 4.19(2H,q,J=7.1),4.66(1H,quintet,J=7.3), 5.17(1H,d,J=7.3), 5.84(2H,s),6.92(2H,d,J=8.8), 7.45(2H,d,J=8.3),7.89(2H,d, J=8.3),7.93(2H,d,J=8.8)

Example 57

N-[4-[5-(4-Pivaloyloxyphenyl)tetrazol-2-ylmethyl]-benzoyl]-L-alanine

N-[4-[5-(4-Hydroxyphenyl)tetrazol-2-ylmethyl]benzoyl]-L-alanine ethyl ester (240 mg), obtained in reference example 8, was added to a solution of aqueous 10% sodium hydroxide (0.48 ml) in methanol (10 ml), and the mixture was allowed to stand at room temperature for 15 h. After the methanol was evaporated, acetone (5 ml) and $H_2O$ (5 ml) were added to the residue. Pivaloyl chloride (72.3 mg) was added dropwise to the solution over 10 min under ice cooling, and stirring was continued for 1 h at the same temperature. After the acetone was evaporated, the residue was acidified with dilute hydrochloric acid, extracted with ethyl acetate, dried, and evaporated to dryness. The residue was purified by column chromatography on silica gel with chloroform-methanol (100/4–20) as an elute and recrystallization from ethyl acetate-hexane gave 81 mg (30%) of the title compound.

m.p.: 192°–195° C.

I.R. $v_{KBr}$ cm$^{-1}$: 1750,1650,1640,1120

N.M.R.(DMSO-d$_6$) δ: 1.28–1.31(12H,m),3.95–4.15(1H,m),6.06(2H,s), 7.29(2H,d,J=8.5),7.48(2H,d,J=8.3),7.85(2H,d,J=8.3), 8.07–8.12(3H,m)

The following compounds were obtained from corresponding starting materials by the same procedures as reference example 8 and example 57.

Example 58

N-[4-[5-(4-pivaloyloxyphenyl)tetrazol-2-ylmethyl]-benzoyl]glycine yield 17% m.p.: 230°–232° C.

I.R. $v_{KBr}$ cm$^{-1}$: 1755,1660,1640,1620,1120

N.M.R.(DMSO-d$_6$) δ: 1.31(9H,s),3.69(2H,d,J=4.6), 6.06(2H,s), 7.29(2H,d,J=8.5),7.47(2H,d,J=8.0),7.87(2H,d,J=8.0), 8.09(2H,d,J=8.5),8.17(1H,brs)

Example 59

N-[4-[5-(4-pivaloyloxyphenyl)tetrazol-2-ylmethyl]-benzoyl]-L-Proline yield 40% m.p.: 145°–148° C.

I.R. $v_{KBr}$ cm$^{-1}$: 1750,1610,1115

N.M.R.(CDCl$_3$) δ: 1.36(9H,s),1.60–2.70(4H,m), 3.30–3.55(2H,m), 4.60–4.70(1H,m),5.78(2H,s),7.16(2H,d,J=8.6), 7.30–7.60(4H,m),8.13(2H,d,J=8.6)

Example 60

Sodium N-[4-[5-(4-pivaloyloxyphenyl)tetrazol-2-ylmethyl]-benzoyl]-L-phenylalaninate yield 47.3% m.p.: 124°–126° C.

I.R. $v_{KBr}$ cm$^{-1}$: 1755,1650,1470,1205,1120

N.M.R.(DMSO-d$_6$) δ: 1.32(9H,s),3.00–3.25(2H,m), 4.40–4.53(1H,m), 6.05(2H,s),7.12–7.23(5H,m),7.29(2H,d,J=8.5), 7.46(2H,d,J=8.0),7.78(2H,d,J=8.0),8.09(2H,d,J=8.5)

Example 61

N-[4-[5-(4-Pivaloyloxyphenyl)tetrazol-2-ylmethyl]-benzoyl]-L-glutamic acid yield 50% m.p.: 121°–123° C.

I.R. $v_{KBr}$ cm$^{-1}$: 1750,1720,1640,1465,1205,1120

N.M.R.(DMSO-d$_6$) δ: 1.32(9H,s),1.91–2.13(2H,m), 2.34(2H,t,J=7.3), 4.30–4.45(1H,m),6.08(2H,s),7.29(2H,d,J=8.5), 7.51(2H,d,J=8.1),7.90(2H,d,J=8.1),8.10(2H,d,J=8.5), 8.55(1H,d,J=8.0)

Example 62

N-[4-[5-(4-Pivaloyloxyphenyl)tetrazol-2-ylmethyl]-benzoyl]-DL-methionine yield 32% m.p.: 109°–111° C.

I.R. $v_{KBr}$ cm$^{-1}$: 1750,1650,1465,1205,1120

N.M.R.(DMSO-d$_6$) δ: 1.32(9H,s),2.00–2.10(5H,m), 2.40–2.60(2H,m), 4.43–4.58(1H,m),6.07(2H,s),7.29(2H,d,J=8.5), 7.50(2H,d,J=8.3),7.90(2H,d,J=8.3), 8.09(2H,d,J=8.5),8.64(1H,d,J=7.8)

Example 63

N-[2-[5-(4-Pivaloyloxyphenyl)tetrazol-2-ylmethyl]-benzoyl]glycine yield 61% amorphous powder

I.R. $v_{KBr}$ cm$^{-1}$: 1755,1470,1120

N.M.R.(CDCl$_3$) δ: 1.36(9H,s),4.27(2H,d,J=5.3),6.11(2H,s), 7.14(2H,d,J=8.5),7.28–7.35(1H,m),7.37–7.50(2H,m), 7.55–7.65(1H,m),8.10(2H,d,J=8.5)

Example 64

N-[4-[5-(4-Pivaloyloxyphenyl)tetrazol-2-ylmethyl]-benzoyl]-L-valine benzyl ester

4-[5-(4-Hydroxyphenyl)tetrazol-2-ylmethyl]benzoic acid (296 mg), which was obtained from a corresponding starting material by the same procedures as reference example 7, L-valine benzyl ester hydrochloride (243.5 mg), 1-hydroxybenzotriazole (153 mg), and N-methylmorpholine (101 mg) were dissolved in a mixed solution of dichloromethane (5 ml) and dimethylformamide (2 ml). Dicyclohexylcarbodiimide (206 mg) was added to the solution under ice cooling, and stirring was continued for 15 h at room temperature. After the dichloromethane was evaporated, ethyl acetate was added and the resulting precipitate was filtered off. The ethyl acetate layer was washed succesively with an aqueous 10% sodium hydrogencarbonate solution, 1N hydrochloric acid, and water, dried, and evaporated to dryness. The residue was dissolved in dichloromethane (10 ml), and triethylamine (101 mg) and a catalytic amount of 4-dimethylaminopyridine were added to the solution. A solution of pivaloyl chloride (120.5 mg) in dichloromethane (2 ml) was added dropwise to the solution over 10 min under ice cooling. After the reaction was completed, the reaction mixture was washed with water, dried, and evaporated to dryness. The residue was purified by column chromatography on silica gel with ethyl acetate-hexane (1/1) as an eluate to give 450 mg (80%) of the title compound.

m.p.: 157°–159° C.

I.R. $\nu_{KBr}$ cm$^{-1}$: 1740,1650,1460,1120

N.M.R.(DMSO-d$_6$) δ: 0.92(3H,d,J=6.8),0.95(3H,d,J=6.8),1.32(9H,s), 2.15–2.23(1H,m),4.32(1H,t,J=7.5), 5.14(2H,ABq,J=12.5),6.08(2H,s),7.28–7.35(7H,m), 7.51(2H,d,J=8.3),7.89(2H,d,J=8.0), 8.09(2H,d,J=8.3), 8.65(1H,d,J=7.5)

The following compounds were obtained from corresponding starting materials by the same procedures as example 64.

Example 65

6-[N-[4-[5-(4-Pivaloyloxyphenyl)tetrazol-2-ylmethyl]-benzoyl]amino]caproic acid benzyl ester yield 80% m.p.: 105°–108° C.

I.R. $\nu_{KBr}$ cm$^{-1}$: 3325,1740,1735,1635,1460,1205,1165, 1120

N.M.R.(DMSO-d$_6$) δ: 1.37(9H,s),1.50–1.75(6H,m), 2.37(2H,t,J=7.2), 3.40–3.50(2H,m),5.10(2H,s),5.83(2H,s), 6.15(1H,brs), 7.17(2H,d,J=8.5),7.33(5H,s),7.46(2H,d,J=8.0), 7.78(2H,d,J=8.0),8.14(2H,d,J=8.5)

Example 66

N-[2-(Benzyloxycarbonylamino)ethyl]-4-[5-(4-pivaloyloxyphenyl)tetrazol-2-ylmethyl]benzamide yield 27.6% m.p.: 160°–162° C.

I.R. $\nu_{KBr}$ cm$^{-1}$: 1750,1695,1540,1465,1280,1120

N.M.R.(CDCl$_3$) δ: 1.36(9H,s),3.40–3.60(4H,m),5.08(2H,s),5.22(1H,brs), 5.83(2H,s),7.08(1H,brs),7.17(2H,d,J=8.8), 7.28(5H,s), 7.43(2H,d,J=8.3),7.78(2H,d,J=8.3),8.14(2H,d,J=8.8)

Example 67

N-[4-[5-(4-Pivaloyloxyphenyl)tetrazol-2-ylmethyl]-benzoyl]-L-valine

A solution of N-[4-[5-(4-pivaloyloxyphenyl)tetrazol-2-ylmethyl]benzoyl]-L-valine benzyl ester (242 mg), obtained in example 64, in methanol (20 ml) was hydrogenated over 5% palladium carbon (50 mg). After the reaction was completed, the catalyst was filtered off, and the filtrate was evaporated. The residue was triturated with ethyl acetate to give the title compound as an amorphous powder in a quantitative yield.

I.R. $\nu_{KBr}$ cm$^{-1}$: 1750,1650,1465,1205,1120

N.M.R.(DMSO-d$_6$) δ: 0.94(3H,d,J=6.6),0.95(3H,d,J=6.6),1.32(9H,s), 2.16–2.25(1H,m),4.25–4.32(1H,m), 6.08(2H,s), 7.29(2H,d,J=8.5),7.49(2H,d,J=8.0),7.89(2H,d,J=8.0), 8.09(2H,d,J=8.5),8.42(1H,d,J=8.5)

The following compounds were obtained from corresponding starting materials by the same procedures as example 67.

Example 68

6-[N-[4-[5-(4-Pivaloyloxyphenyl)tetrazol-2-ylmethyl]benzoyl]amino]caproic acid yield 100% m.p.: 131°–132° C.

I.R. $\nu_{KBr}$ cm$^{-1}$: 3400,1750,1640,1465,1205,1120

N.M.R.(DMSO-d$_6$) δ: 1.32(9H,s),1.20–1.40(2H,m), 1.40–1.60(4H,m), 2.18(2H,t,J=7.0),3.23(2H,q,J=6.1), 6.06(2H,s), 7.29(2H,d,J=8.5),7.48(2H,d,J=8.3),7.85(2H,d,J=8.3), 8.09(2H,d,J=8.5),8.45(1H,t,J=6.1)

Example 69

2-Phenyl-2-[5-(4-pivaloyloxyphenyl)tetrazol-2-yl]acetic acid yield 100% m.p.: 154°–157° C.

I.R. $\nu_{KBr}$ cm$^{-1}$: 3450,1750,1470,1205,1120

N.M.R.(DMSO-d$_6$) δ: 1.32(9H,s),7.20(1H,s),7.30(2H,d,J=8.5), 7.43–7.52(3H,m),7.62–7.68(2H,m),8.09(2H,d,J=8.5)

Example 70

N-[2-Phenyl-2-[5-(4-pivaloyloxyphenyl)tetrazol-2-yl]acetyl]glycine

The title compound was obtained from a corresponding starting material by the same procedure as example 41 and example 67 in 70% yield.

m.p.: 86°–93° C.

I.R. $\nu_{KBr}$ cm$^{-1}$: 1750,1690,1465,1205,1120

N.M.R.(DMSO-d$_6$) δ: 1.32(9H,s),3.84(2H,s),7.04(1H,s), 7.29(2H,d,J=8.5), 7.45–7.48(3H,m),7.65–7.66(2H,m), 8.07(2H,d,J=8.5), 8.77(1H,brs)

Example 71

N-(2-Aminoethyl)-4-[5-(4-pivaloyloxyphenyl)-tetrazol-2-ylmethyl]benzamide Hydrochloride A solution of N-[2-(benzyloxycarbonylamino)ethyl]-4-[5-(4-pivaloyloxyphenyl)tetrazol-2-ylmethyl]benzamide (120 mg), which was obtained in example 66, and hydrogenchloride (0.052 ml,4N solution in ethyl acetate) in methanol (5 ml) was hydrogenated over 5% palladium carbon. The catalyst was filtered off, and the filtrate was evaporated to give 100 mg of the title compound.

m.p.: 230°–232° C.

I.R. $\nu_{KBr}$ cm$^{-1}$: 3400,3300,1750,1640,1460,1210,1120,

N.M.R.(DMSO-d$_6$) δ: 1.32(9H,s),2.98(2H,brs),3.52(2H,q,J=5.9), 6.08(2H,s),7.30(2H,d,J=8.3),7.49(2H,d,J=8.0), 7.95(2H,d,J=8.0),8.09(2H,d,J=8.3),8.10(3H,brs), 8.79(1H,t,J=5.9)

Example 72

4-[2-(2-Hydroxyethyl)tetrazol-5-yl]phenyl pivalate

To a solution of 4-[2-[2-(4-methoxybenzyloxy)ethyl]tetrazol-5-yl ]phenyl pivalate (2.0 g), obtained in example 41, in a mixed solution of dichloromethane (60 ml) and water (3 ml) was added dichlorodicyanobenzoquinone (1.21 g), and stirring was continued for 15 h at room temperature. The precipitate was filtered off, and the filtrate was dried and evaporated to dryness. The residue was purified by column chromatography on silica gel with ethyl acetate-hexane (1/1) as an eluate and recrystallization from hexane gave 1.07 g (75 %) of the title compound.

m.p.: 92°–95° C.

I.R. $\nu_{KBr}$ cm$^{-1}$: 3375,1750,1465,1120

N.M.R.(CDCl$_3$) δ: 1.37(9H,s),2.64(1H,t,J=5.1),4.22(2H, q,J=5.1), 4.79(2H,t,J=5.1),7.19(2H,d,J=8.8),8.14(2H,d,J=8.8)

The following compounds were obtained from corresponding starting materials by the same procedures as example 72.

Example 73

4-[2-(4-Hydroxybutyl)tetrazol-5-yl]phenyl pivalate yield 80% m.p.: 86°–89° C.

I.R. ν$_{KBr}$ cm$^{-1}$: 3400,1750,1460,1210,1120

N.M.R.(CDCl$_3$) δ: 1.37(9H,s),1.52(1H,brs), 1.60–1.70(2H,m), 2.12–2.25(2H,m),3.65–3.75(2H,m), 4.70(2H,t,J=7.0), 7.19(2H,d,J=8.5),8.16(2H,d,J=8.5)

Example 74

4-[2-(5-Hydroxypentyl)tetrazol-5-yl]phenyl pivalate yield 78% m.p.: 92°–95° C.

I.R. ν$_{KBr}$ cm$^{-1}$: 3400,1750,1460,1205,1120

N.M.R.(CDCl$_3$) δ: 1.37(9H,s),1.40–1.70(5H,m),2.11(2H, quintet,J=7.1), 3.66(2H,t,J=6.2),4.66(2H,t,J=7.1),7.19(2H, d,J=8.8), 8.16(2H,d,J=8.8)

Example 75

4-[2-(4-Hydroxybenzyl)tetrazol-5-yl]phenyl pivalate yield 14.7% m.p.: 165°–168° C.

I.R. ν$_{KBr}$ cm$^{-1}$: 1758,1470,1120

N.M.R.(CDCl$_3$) δ: 1.36(9H,s),5.15(1H,s),5.70(2H,s), 6.82(2H,d,J=8.6) 7.17(2H,d,J=8.6),7.32(2H,d,J=8.6), 8.14(2H,d,J=8.6)

Example 76

4-[2-(4-Aminobenzyl)tetrazol-5-yl]phenyl pivalate

A solution of 4-[2-(4-nitrobenzyl)tetrazol-5-yl]phenyl pivalate (500 mg), obtained in example 25, in methanol was hydrogenated over 5 % palladium carbon. After the solvent was evaporated in vacuo, the residue was purified by column chromatography on silica gel with ethyl acetate-hexane (1/2) as an eluate. Recrystallization from ethyl acetate-hexane gave 190 mg of the title compound.

m.p.: 180°–182° C.

I.R. ν$_{KBr}$ cm$^{-1}$: 3470,3350,1750,1470,1210,1130

N.M.R.(CDCl$_3$) δ: 1.36(9H,s),3.73(2H,s),5.66(2H,s), 6.66(2H,d,J=8.5), 7.16(2H,d,J=8.8),7.25(2H,d,J=8.5), 8.14(2H,d,J=8.8)

The following compounds were obtained from corresponding starting materials by the same procedures as example 76.

Example 77

4-[2-(3-Aminobenzyl)tetrazol-5-yl]phenyl pivalate yield 62.9% m.p.: 143°–146° C.

I.R. ν$_{KBr}$ cm$^{-1}$: 1740,1460,1210,1120

N.M.R.(CDCl$_3$) δ: 1.37(9H,s),5.70(2H,s),6.64–6.80(3H, m), 7.12–7.19(3H,m),8.16(2H,d,J=8.6)

Example 78

4-[2-(2-Aminobenzyl)tetrazol-5-yl]phenyl pivalate m.p.: 128°–131° C.

I.R. ν$_{KBr}$ cm$^{-1}$: 3475,3400,1750,1465,1205,1120

N.M.R.(CDCl$_3$) δ: 1.36(9H,s),4.37(2H,s),5.73(2H,s), 6.74(1H,d,J=8.0), 6.80(1H,t,J=7.6),7.15–7.21(3H,m), 7.37(1H,d,J=7.6), 8.12(2H,d,J=8.5)

Example 79

4-[2-[2-(Methylsulfonylamino)benzyl]tetrazol-5-yl]phenyl pivalate

Methanesulfonyl chloride (114.5 mg) was added to a solution of 4-[2-(2-aminobenzyl)tetrazol-5-yl]phenyl pivalate (0.351 g), obtained in example 78, and pyridine (79 mg) in dichloromethane (2 ml) under ice cooling, and stirring was continued for 15 h. The mixture was washed with water, dried and evaporated to dryness. The residue was purified by column chromatography on silica gel with ethyl acetate-hexane (1/2) as an eluate. Recrystallization from ethyl acetate-hexane gave 300 mg (70%) of the title compound.

m.p.: 162°–163° C.

I.R. ν$_{KBr}$ cm$^{-1}$: 3275,1750,1465,1110

N.M.R.(CDCl$_3$) δ: 1.37(9H,s),3.10(3H,s),5.91(2H,s), 7.18(2H,d,J=8.6), 7.22–7.27(1H,m),7.37–7.43(2H,m), 7.53(1H,d,J=7.8), 8.00(1H,brs),8.12(2H,d,J=8.6)

Example 80

5-(4-Pivaloyloxyphenyl)-2-tetrazoleacetic acid 4-(2-t-Butoxycarbonylmethyltetrazol-5-yl)phenyl pivalate (0.8 g), obtained in example 10, was dissolved in trifluoroacetic acid (4 ml), and stirring was continued for 4 h under ice cooling. After evaporating, the residue was crystallized from hexane to give 660 mg (97%) of the title compound.

m.p.: 208°–212° C.

I.R. ν$_{KBr}$ cm$^{-1}$: 1750,1725,1120

N.M.R.(DMSO-d$_6$) δ: 1.33(9H,s),5.74(2H,s),7.32(2H,d, J=8.8), 8.12(2H,d,J=8.8)

The following compounds were obtained from corresponding starting materials by the same procedures as example 80.

Example 81

2-[5-(4-Pivaloyloxyphenyl)tetrazol-2-ylmethyl]-phenoxyacetic acid yield 98.2% m.p.: 74°–75° C.

I.R. ν$_{KBr}$ cm$^{-1}$: 3100–2900,1750,1210,1125

N.M.R.(CDCl$_3$) δ: 1.37(9H,s),4.71(2H,s),5.90(2H,s), 6.87(1H,d,J=8.0), 7.09(1H,t,J=8.0),7.18(2H,d,J=8.5), 7.41(1H,t,J=8.0), 7.50(1H,d,J=8.0),8.14(2H,d,J=8.5)

Example 82

3-[5-(4-Pivaloyloxyphenyl)tetrazol-2-ylmethyl]-phenoxyacetic acid yield 83.6% m.p.: 150°–152° C.

I.R. $v_{KBr}$ cm$^{-1}$: 3000–2800,1750,1715,1465,1270,1205, 1118

N.M.R.(CDCl$_3$) δ: 1.37(9H,s),4.67(2H,s),5.77(2H,s), 6.92(1H,d,J=7.9), 6.98(1H,brs),7.06(1H,d,J=7.9),7.17(2H, d,J=8.9), 7.33(1H,t,J=7.9),8.14(2H,d,J=8.9)

Example 83

4-[5-(4-Pivaloyloxyphenyl )tetrazol-2-ylmethyl ]phenoxyacetic acid yield 84.6% m.p.: 156°–157° C.

I.R. $v_{KBr}$ cm$^{-1}$: 3000–2800,1735,1220,1190,1108

N.M.R.(CDCl$_3$) δ: 1.37(9H,s),4.67(2H,s),5.74(2H,s), 6.93(2H,d,J=8.7), 7.17(2H,d,J=8.6),7.40(2H,d,J=8.7), 8.14(2H,d,J=8.6)

Example 84

4-[2-[2- (2-Aminoethoxy )benzyl]tetrazol-5-yl]phenyl pivalate Hydrochloride

Hydrogen chloride (10 ml, 4N solution in ethyl acetate) was added to 4-[2-[2-[2-(t-butoxycarbonylamino)ethoxy]benzyl]tetrazol -5-yl]phenyl pivalate (200 mg), obtained in example 34, and the solution was allowed to stand in an ice box for 15 h. After the ethyl acetate was concentrated in vacuo, the resulting crystals were filtered and dried to give 160 mg (93%) of the title compound.

m.p.: 96°–98° C.

I.R. $v_{KBr}$ cm$^{-1}$: 3200–2800,1755,1470,1120

N.M.R. (DMSO-d$_6$) δ: 1.32(9H,s),3.21(2H,brs),4.24(2H, t,J=4.8), 6.09(2H,s),7.00(1H,t,J=7.5),7.09(1H,d,J=7.5), 7.19(1H,d,J=7.5),7.29(2H,d,J=8.5),7.38(1H,t,J=7.5), 8.09(2H,d,J=8.5),8.31(3H,brs)

The following compounds were obtained from corresponding starting materials by the same procedures as example 84.

Example 85

4-[2-[3-(2-Aminoethoxy)benzyl]tetrazol-5-yl]phenyl pivalate Hydrochloride m.p.: 163°–165° C.

I.R. $v_{KBr}$ cm$^{-1}$: 3200–2800,1755,1470,1120

N.M.R.(DMSO-d$_6$) δ: 1.32(9H,s),3.19(2H,t,J=4.9), 4.19(2H,t,J=4.9), 5.99(2H,s),6.97(1H,s),7.00–7.05(2H,m), 7.30(2H,d,J=8.8),7.36(1H,t,J=8.0), 8.09(2H,d,J=8.0), 8.10(3H,brs)

Example 86

4-[2-[4-(2-Aminoethoxy)benzyl]tetrazol-5-yl]phenyl pivalate Hydrochloride m.p.: 216°–219° C.

I.R. $v_{KBr}$ cm$^{-1}$: 3100,2900,1755,1465,1260,1120

N.M.R.(DMSO-d$_6$) δ: 1.32(9H,s),3.19(2H,brs),4.17(2H,t, J=5.2), 5.92(2H,s),7.02(2H,d,J=8.5),7.29(2H,d,J=8.5), 7.42(2H,d,J=8.5),8.05(3H,brs),8.08(2H,d,J=8.5)

Example 87

4-[2-[4-(Glycylamino)benzyl]tetrazol-5-yl]phenyl pivalate Hydrochloride m.p.: 250° C. (dec.)

I.R. $v_{KBr}$ cm$^{-1}$: 3200,2800,1758,1695,1465,1125

N.M.R.(DMSO-d$_6$) δ: 1.32(9H,s),3.79(2H,s),5.95(2H,s), 7.29(2H,d,J=8.5), 7.43(2H,d,J=8.3),7.64(2H,d,J=8.3), 8.09(2H,d,J=8.5), 8.22(3H,brs),10.78(1H,s)

Example 88

4-[2-[3-(2-Aminoethoxy)benzyl]tetrazol-5-yl]-2-methoxyphenyl pivalate Hydrochloride m.p.: 118°–120° C.

I.R. $v_{KBr}$ cm$^{-1}$: 1760,1480,1270,1125

N.M.R.(DMSO-d$_6$) δ: 1.31(9H,s),3.19(2H,t,J=4.9), 3.86(3H,s), 4.18(2H,t,J=4.9),6.01(2H,s),7.01–7.04(3H,m), 7.24(1H,d,J=8.3),7.36(1H,t,J=8.3),7.64–7.65(2H,m), 8.26(3H,s)

Example 89

4-[2-[3-(3-Aminopropyl)benzyl]tetrazol-5-yl]phenyl pivalate Hydrochloride m.p.: 176°–179° C.

I.R. $v_{KBr}$ cm$^{-1}$: 1750,1460,1200,1120

N.M.R.(DMSO-d$_6$) δ: 1.32(9H,s),1.85(2H,quintet,J=7.3), 2.65(2H,t,J=7.5), 2.77(2H,t,J=7.3),5.97(2H,s), 7.22–7.40(6H,m), 7.90(3H,brs),8.10(2H,d,J=8.5)

Example 90

4-[2-(4-Methylaminobenzyl)tetrazol-5-yl]phenyl pivalate yield 77% m.p.: 144°–146° C.

I.R. $v_{KBr}$ cm$^{-1}$: 3425,1740,1530,1465,1210,1120

N.M.R.(CDCl$_3$) δ: 1.36(9H,s),2.82(3H,s),3.82(1H,brs), 5.66(2H,s), 6.57(2H,d,J=8.8),7.15(2H,d,J=8.8),7.28(2H,d, J=8.8), 8.13(2H,d,J=8.8)

Example 91

4-[1-(4-Methylaminobenzyl)tetrazol-5-yl]phenyl pivalate yield 68% m.p.: 111°–115° C.

I.R. $v_{KBr}$ cm$^{-1}$: 3410,1750,1530,1480,1220,1105

N.M.R.(CDCl$_3$) δ: 1.37(9H,s),2.81(3H,s),3.81(1H,brs), 5.48(2H,s), 6.53(2H,d,J=8.5),7.00(2H,d,J=8.5),7.23(2H,d, J=8.8), 7.64(2H,d,J=8.8)

Example 92

4-[2-(2-Aminoethyl)tetrazol-5-yl]phenyl pivalate Hydrochloride yield 16% m.p.: 220° C.

I.R. $\nu_{KBr}$ cm$^{-1}$: 3200–2800,1760,1460,1200

N.M.R. (DMSO-d$_6$) δ: 1.33(9H,s),3.50(2H,t,J=5.5), 5.02(2H,t,J=5.5), 7.33(2H,d,J=8.3),8.14(2H,d,J=8.3), 8.20(3H,s)

Example 93

5-[5-(4-Pivaloyloxyphenyl)tetrazol-2-yl]valeric acid

4-[2-(5-Hydroxypentyl)tetrazol-5-yl]phenyl pivalate (180 mg), obtained in example 74, and sodium periodate (348.7 mg) were dissolved in a mixed solution of carbon tetrachloride (4 ml), acetonitrile (4 ml) and H$_2$O (6 ml). Ruthenium dichloride hydrate (4 mg) was added to the solution, and stirring was continued for 4 h at room temperature. The mixture was extracted with chloroform, dried and evaporated to dryness. The residue was recrystallized from ethyl acetate-hexane to give 150 mg (80%) of the title compound.

m.p.: 129°–131° C.

I.R. $\nu_{KBr}$ cm$^{-1}$: 1750,1710,1460,1120

N.M.R.(CDCl$_3$) δ: 1.37(9H,s),1.73(2H,quintet,J=7.4), 2.14(2H,quintet,J=7.4),2.44(2H,t,J=7.4), 4.67(2H,t,J=7.4), 7.19(2H,d,J=8.3),8.16(2H,d,J=8.3)

Example 94

4-[2-[2-(4-Guanidinobenzoyloxy)ethyl]tetrazol-5-yl]phenyl pivalate Acetate

4-Guanidinobenzoyl chloride hydrochloride (468 mg) was added to a solution of 4-[2-(2-hydroxyethyl)tetrazol-5-yl]phenyl pivalate (290 mg), obtained in example 72, in pyridine (5 ml) under ice cooling, and stirring was continued for 1.5 h at the same temperature. The mixture was added to ether (50 ml), and the precipitate was filtered and washed with ether (30 ml) 2 times. To it was added aqueous saturated sodium bicarbonate (10 ml), and stirring was continued for 1 h at room temperature. The resulting precipitate was filtered and washed with water to give the carbonate. The salt was dissolved in acetic acid (1 ml), and the solution was purified by column chromatography on silica gel with ethyl acetate-acetic acid-water (40/10/3) to give 340 mg of the title compound as an amorphous powder.

I.R. $\nu_{KBr}$ cm$^{-1}$: 1750,1720,1680,1280,1120

N.M.R.(CDCl$_3$) δ: 1.36(9H,s),1.98(3H,s),4.86(2H,brs), 5.03(2H,brs), 7.18(2H,d,J=8.5),7.23(2H,d,J=8.5),7.96(2H, d,J=8.5), 8.14(2H,d,J=8.5)

Example 95

4-[2-[2-(4-Guanidinobenzoylamino)ethyl]tetrazol-5-yl]phenyl pivalate Acetate 4-[2-(2-Aminoethyl)tetrazol-5-yl]phenyl pivalate hydrochloride (0.326 g), obtained in example 92, was suspended in pyridine (10 ml) with stirring. 4-Guanidinobenzoyl chloride hydrochloride (0,468 g) was added to the suspension under ice cooling. After stirring for 10 min, the reaction mixture became to a clear solution. After stirring for 2 h, this solution was added to ether (50 ml). The supernatant was discarded by decantation to give the resulting precipitate which was washed with ether 2 times. To the precipitate was added aqueous saturated sodium bicarbonate. The resulting precipitate was filtered, washed with water, and dried. This precipitate was dissolved in acetic acid (5 ml). This solution was purified by column chromatography on silica gel with ethyl acetate-acetic acid-H$_2$O (80/20/6) as an eluate. The elution was evaporated in vacuo and triturated with ether to give 0.36 g of the title compound as a powder.

m.p.: 210° C. (dec.)

I.R. $\nu_{KBr}$ cm$^{-1}$: 1755,1700,1540,1210,1120

N.M.R.(CDCl$_3$) δ: 1.32(9H,s),1.73(3H,s),3.81(2H,brs), 4.90(2H,brs), 7.09(2H,d,J=8.5),7.29(2H,d,J=8.5),7.73(2H, d,J=8.5), 8.09(2H,d,J=8.5)

Example 96

4-[1-(4-Isopropylbenzyl)tetrazol-5-yl]phenyl pivalate

Phosphorus pentachloride (0,249 g) was added to a solution of N-(4-isopropylbenzyl)-4-pivaloyloxybenzamide (0.353 g) in dichloeomethane (5 ml) under ice cooling, and stirring was continued for 2 h. This reaction mixture was added dropwise to a solution of sodium azide (0.78 g) in H$_2$O (10 ml) at room temperature, and stirring was continued for 1 h. The mixture was extracted with chloroform, and the extract was washed with water, dried and evaporated to dryness. The residue was purified by column chromatography on silica gel with ethyl acetate-benzene (5/100) as an eluate and crystallization from hexane gave 0.2 g of the title compound.

m.p.: 111°–113° C.

I.R. $\nu_{KBr}$ cm$^{-1}$: 1750,1480,1120

N.M.R.(CDCl$_3$) δ: 1.23(6H,d,J=6.8),1.37(9H,s),2.28(1H, septet,J=6.8), 5.57(2H,s),7.10(2H,d,J=8.3),7.21(2H,d,J= 8.3), 7.23(2H,d,J=8.5),7.63(2H,d,J=8.5)

Example 97

4-[2-[4-(Ethylmethylamino)benzyl]tetrazol-5-yl]phenyl pivalate

A mixture of 4-[2-(4-methylaminobenzyl)tetrazol-5-yl]phenyl pivalate (150 mg), obtained in example 90, potassium bicarbonate (46 mg) and iodoethane (84 mg) in dimethylformamide (3 ml) was heated with stirring at 60° C. for 24 h. After cooling, the mixture was poured into ice water and extracted with ethyl acetate. The extract was washed with water, dried and evaporated to dryness. The residue was purified by column chromatography on silica gel with ethyl acetate-hexane (1/4) as an eluate and recrystallization from ethyl acetate-hexane gave 71 mg (44.6%) of the title compound.

m.p.: 122°–125° C.

I.R. $\nu_{KBr}$ cm$^{-1}$: 1755,1620,1530,1460,1200,1110

N.M.R.(CDCl$_3$) δ: 1.10(3H,t,J=7.1),1.36(9H,s),2.90(3H, s), 3.38(2H,q,J=7.1),5.67(2H,s),6.67(2H,d,J=8.8), 7.15(2H, d,J=8.8),7.31(2H,d,J=8.8),8.14(2H,d,J=8.8)

The following compounds were obtained from corresponding alkyl halides by the same procedures as example 97.

Example 98

4-[2-[4-(Methylpropylamino)benzyl]tetrazol-5-yl]phenyl pivalate yield 48.2% m.p.: 105°–107° C.

I.R. $\nu_{KBr}$ cm$^{-1}$: 1760,1620,1530,1460,1210,1120

N.M.R.(CDCl$_3$) δ: 0.90(3H,t,J=7.3),1.36(9H,s), 1.53–1.64(2H,m), 2.92(3H,s),3.26(2H,t,J=7.1),5.66(2H,s), 6.64(2H,d,J=8.8),7.15(2H,d,J=8.8), 7.31(2H,d,J=8.8), 8.13(2H,d,J=8.8)

Example 99

4-[1-[4-(Dimethylamino)benzyl]tetrazol-5-yl]phenyl pivalate yield 26% m.p.: 135°–139° C.

I.R. $\nu_{KBr}$ cm$^{-1}$: 1765,1620,1530,1480,1220,1110

N.M.R.(CDCl$_3$) δ: 1.37(9H,s),2.94(6H,s),5.50(2H,s), 6.64(2H,d,J=8.8), 7.05(2H,d,J=8.8),7.21(2H,d,J=8.8), 7.64(2H,d,J=8.8)

Example 100

4-[2-[3-(Dimethylamino)benzyl]tetrazol-5-yl]phenyl pivalate yield 7.9% m.p.: 125°–127° C.

I.R. $\nu_{KBr}$ cm$^{-1}$: 1740,1600,1470,1200,1120

N.M.R.(CDCl$_3$) δ: 1.37(9H,s),2.95(6H,s),5.74(2H,s), 6.68–6.87(3H,m), 7.15–7.23(3H,m),8.15(2H,d,J=8.8)

Example 101

4-[2-[2-(Dimethylamino)benzyl]tetrazol-5-yl]phenyl pivalate yield 26.4% m.p.: 65°–67° C.

I.R. $\nu_{KBr}$ cm$^{-1}$: 1745,1460,1200,1160,1120

N.M.R. (CDCl$_3$) δ: 1.37(9H,s),2.74(6H,s),5.99(2H,s), 7.03–7.35(6H,m), 8.16(2H,d,J=8.6)

The structures of these compounds obtained in the foregoing examples are shown in the following Table 1.

TABLE 1

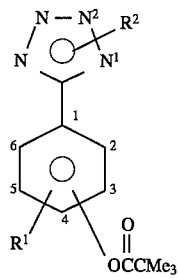

| Example No. | the position of —OCCMe$_3$ on phenyl ring | R$^1$ | R$^2$ |
|---|---|---|---|
| 1 | 2 | H | H |
| 2 | 3 | H | H |
| 3 | 4 | H | H |
| 4 | 4 | 3-Me | H |
| 5 | 4 | 3-OMe | H |
| 6 | 4 | H | 2-C$_6$H$_4$-CHMe$_2$ |
| 7 | 4 | 3-NMe$_2$ | 2-CH$_2$-C$_6$H$_4$-NMe$_2$ |
| 8 | 4 | 3-NMe$_2$ | 2-CH$_2$-C$_6$H$_4$-CO$_2$H |
| 9 | 4 | H | 2-CH$_2$-C$_6$H$_5$ |
| 10 | 4 | H | 2-CH$_2$CO$_2$t-Bu |

TABLE 1-continued
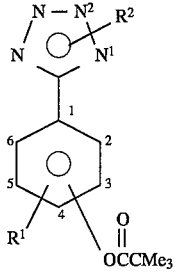
| Example No. | the position of $-OCCMe_3$ (O) on phenyl ring | R¹ | R² |
|---|---|---|---|
| 11 | 4 | H | 2-CH₂CONH—⌬ |
| 12 | 4 | H | 2-CH₂CON(piperidinyl) |
| 13 | 4 | H | 2-CH₂—⌬—OMe |
| 14 | 4 | H | 2-CH₂CH₂—⌬ |
| 15 | 4 | H | 2-CH₂OCH₂—⌬ |
| 16 | 4 | H | 2-CH₂—⌬—NMe₂ |
| 17 | 4 | H | 2-CH₂—⌬—CF₃ |
| 18 | 4 | H | 2-CH₂—⌬—OCH₂—⌬—OMe |
| 19 | 4 | H | 2-CH₂—⌬—CHMe₂ |
| 20 | 4 | H | 2-(CH₂)₃—⌬—OMe |
| 21 | 4 | H | 2-(CH₂)₄—⌬—OMe |

TABLE 1-continued

[Structure: triazole-CH(N¹)(N²=N) attached to phenyl ring numbered 1-6, with R¹ at position 4 and —OC(=O)CMe₃ group]

| Example No. | the position of —OCCMe₃ (O=) on phenyl ring | R¹ | R² |
|---|---|---|---|
| 22 | 2 | H | 2-(CH₂)₄OCH₂—C₆H₄—OMe |
| 23 | 3 | H | 2-(CH₂)₄OCH₂—C₆H₄—OMe |
| 24 | 4 | H | 2-CH₂—C₆H₄—CO₂Me |
| 25 | 4 | H | 2-CH₂—C₆H₄—NO₂ |
| 26 | 4 | H | 2-CH₂—C₆H₄—NO₂ |
| 27 | 4 | H | 2-CH₂—C₆H₄—NO₂ |
| 28 | 4 | H | 2-CH(C₆H₅)(C₆H₅) |
| 29 | 4 | H | 2-CH₂—C₆H₄—COMe |
| 30 | 4 | H | 2-CH₂—C₆H₄—OCH₂CO₂t-Bu |

TABLE 1-continued

[Structure: phenyl ring with position numbers 1-6, bearing at position 1 a CH group connected to a tetrazole ring (N—N²—R², N, N¹), R¹ at position 4 (or other), and —OCCMe₃ (=O) group]

| Example No. | the position of —OCCMe₃ (O=) on phenyl ring | R¹ | R² |
|---|---|---|---|
| 31 | 4 | H | 2-CH₂—[phenyl]—OCH₂CO₂t-Bu (meta) |
| 32 | 4 | H | 2-CH₂—[phenyl]—OCH₂CO₂t-Bu (para) |
| 33 | 4 | H | 2-CH₂—[phenyl]—OCH₂CH₂NHCO₂t-Bu (para) |
| 34 | 4 | H | 2-CH₂—[phenyl]—OCH₂CH₂NHCO₂t-Bu (ortho) |
| 35 | 4 | H | 2-CH₂—[pyridyl-N] |
| 36 | 4 | H | 2-t-Bu |
| 37 | 4 | H | 2-CH₂CHMe₂ |
| 38 | 4 | H | 2-CH₂CH₂NMe₂·HCl |
| 39 | 4 | H | 2-CH₂—[phenyl]—NMeCO₂t-Bu |
| 40 | 4 | H | 1-CH₂—[phenyl]—NMeCO₂t-Bu |
| 41 | 4 | H | 2-CH₂CH₂OCH₂—[phenyl]—OMe |
| 42 | 4 | H | 2-(CH₂)₄OCH₂—[phenyl]—OMe |
| 43 | 4 | H | 2-(CH₂)₅OCH₂—[phenyl]—OMe |

TABLE 1-continued

[Structure: phenyl ring with positions 1-6, bearing at position 1 a CH group connected to a triazole ring (N—N²—N, N¹, R²), and at position 4 bearing R¹ and —OC(=O)CMe₃]

| Example No. | the position of —OCCMe₃ on phenyl ring | R¹ | R² |
| --- | --- | --- | --- |
| 44 | 4 | H | 2-CH₂CH₂—C₆H₄—OMe |
| 45 | 4 | H | 2-CH₂CH₂NHCO₂t-Bu |
| 46 | 4 | H | 2-CH₂—C₆H₄—OCH₂CH₂NMe₂·HCl |
| 47 | 4 | H | 2-CH₂—C₆H₄—CH₂NMe₂ |
| 48 | 4 | 3-OMe | 2-CH₂—C₆H₄—NMe₂ |
| 49 | 4 | 3-Me | 2-CH₂—C₆H₄—NMe₂ |
| 50 | 4 | H | 2-CH₂—C₆H₄—N(pyrrolidinyl) |
| 51 | 4 | H | 2-CH(C₆H₅)—CO₂CH₂—C₆H₅ |
| 52 | 4 | H | 2-CH₂—C₆H₄—CO₂H (ortho) |
| 53 | 4 | H | 2-CH₂—C₆H₄—CH₂CO₂H |
| 54 | 4 | H | 2-CH₂—C₆H₄—CO₂H |

TABLE 1-continued
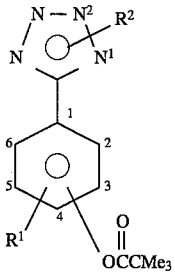
| Example No. | the position of —OCCMe₃ (O=) on phenyl ring | R¹ | R² |
|---|---|---|---|
| 55 | 4 | H | 2-CH₂—⟨phenyl⟩—CO₂H |
| 56 | 4 | 3-OMe | 2-CH₂—⟨phenyl⟩—CO₂H |
| 57 | 4 | H | 2-CH₂—⟨phenyl⟩—CONH—CH(Me)—CO₂H |
| 58 | 4 | H | 2-CH₂—⟨phenyl⟩—CONHCH₂CO₂H |
| 59 | 4 | H | 2-CH₂—⟨phenyl⟩—CON⟨pyrrolidine-CO₂H⟩ |
| 60 | 4 | H | 2-CH₂—⟨phenyl⟩—CONH—CH(CH₂Ph)—CO₂Na |
| 61 | 4 | H | 2-CH₂—⟨phenyl⟩—CONH—CH(CH₂CH₂CO₂H)—CO₂H |
| 62 | 4 | H | 2-CH₂—⟨phenyl⟩—CONH—CH(CH₂SMe)—CO₂H |

TABLE 1-continued

[Structure: tetrazole-CH(N¹R²)(N²) attached at position 1 of phenyl ring; R¹ at indicated position; OC(=O)CMe₃ group on phenyl ring]

| Example No. | the position of —OCCMe₃ (O=) on phenyl ring | R¹ | R² |
|---|---|---|---|
| 63 | 4 | H | 2-CH₂—(phenyl)—CONHCH₂CO₂H |
| 64 | 4 | H | 2-CH₂—(phenyl)—CONH—CH(iPr)—CO₂CH₂—(phenyl) |
| 65 | 4 | H | 2-CH₂—(phenyl)—CONH(CH₂)₅CO₂CH₂—(phenyl) |
| 66 | 4 | H | 2-CH₂—(phenyl)—CONHCH₂CH₂NHCO₂CH₂—(phenyl) |
| 67 | 4 | H | 2-CH₂—(phenyl)—CONH—CH(iPr)—CO₂H |
| 68 | 4 | H | 2-CH₂—(phenyl)—CONH(CH₂)₅CO₂H |
| 69 | 4 | H | 2-CH(CO₂H)—(phenyl) |
| 70 | 4 | H | 2-CH(CONHCH₂CO₂H)—(phenyl) |
| 71 | 4 | H | 2-CH₂—(phenyl)—CONHCH₂CH₂NH₂·HCl |
| 72 | 4 | H | 2-CH₂CH₂OH |
| 73 | 4 | H | 2-(CH₂)₄OH |
| 74 | 4 | H | 2-(CH₂)₅OH |

TABLE 1-continued

[Structure: phenyl ring with position 1 bearing a CH group attached to a 3-membered ring containing N=N-N² with R² on a carbon bearing N¹; position 4 bears R¹ and OC(=O)CMe₃ (OCCMe₃)]

| Example No. | the position of —OCCMe₃ (O=) on phenyl ring | R¹ | R² |
|---|---|---|---|
| 75 | 4 | H | 2-CH₂—(phenyl)—OH |
| 76 | 4 | H | 2-CH₂—(phenyl)—NH₂ (para) |
| 77 | 4 | H | 2-CH₂—(phenyl with NH₂ meta) |
| 78 | 4 | H | 2-CH₂—(phenyl with NH₂ ortho) |
| 79 | 4 | H | 2-CH₂—(phenyl with NHSO₂Me) |
| 80 | 4 | H | 2-CH₂CO₂H |
| 81 | 4 | H | 2-CH₂—(phenyl with OCH₂CO₂H ortho) |
| 82 | 4 | H | 2-CH₂—(phenyl with OCH₂CO₂H meta) |
| 83 | 4 | H | 2-CH₂—(phenyl)—OCH₂CO₂H (para) |
| 84 | 4 | H | 2-CH₂—(phenyl with OCH₂CH₂NH₂·HCl) |

TABLE 1-continued

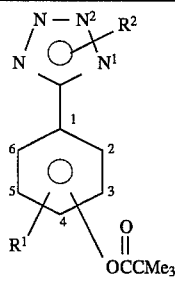

| Example No. | the position of —OCCMe₃ (=O) on phenyl ring | R¹ | R² |
|---|---|---|---|
| 85 | 4 | H | 2-CH₂—(phenyl)-OCH₂CH₂NH₂·HCl (meta) |
| 86 | 4 | H | 2-CH₂—(phenyl)-OCH₂CH₂NH₂·HCl (para) |
| 87 | 4 | H | 2-CH₂—(phenyl)-NHCOCH₂NH₂·HCl |
| 88 | 4 | 3-OMe | 2-CH₂—(phenyl)-OCH₂CH₂NH₂·HCl |
| 89 | 4 | H | 2-CH₂—(phenyl)-(CH₂)₃NH₂·HCl |
| 90 | 4 | H | 2-CH₂—(phenyl)-NHMe |
| 91 | 4 | H | 1-CH₂—(phenyl)-NHMe |
| 92 | 4 | H | 2-CH₂CH₂NH₂·HCl |
| 93 | 4 | H | 2-(CH₂)₄CO₂H |
| 94 | 4 | H | 2-CH₂CH₂OCO—(phenyl)—NH—C(=NH)NH₂ · HOAc |
| 95 | 4 | H | 2-CH₂CH₂NHCO—(phenyl)—NH—C(=NH)NH₂ · HOAc |
| 96 | 4 | H | 1-CH₂—(phenyl)-CHMe₂ |

TABLE 1-continued

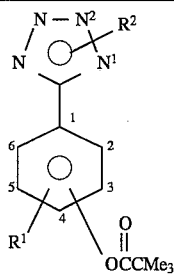

| Example No. | the position of —OCCMe₃ on phenyl ring | $R^1$ | $R^2$ |
|---|---|---|---|
| 97 | 4 | H | 2-CH₂-(phenyl)-NMeEt |
| 98 | 4 | H | 2-CH₂-(phenyl)-NMeCH₂CH₂CH₃ |
| 99 | 4 | H | 1-CH₂-(phenyl)-NMe₂ |
| 100 | 4 | H | 2-CH₂-(phenyl), NMe₂ |
| 101 | 4 | H | 2-CH₂-(phenyl), NMe₂ |

EFFECT

Derivatives of tetrazolylphenyl ester of pivalic acid of the general formura (1) of the present invention, and of the non-toxic salts and acid addition salts thereof, have an inhibitory effect on elastase.

Accordingly, the derivatives of the present invention are useful for treatment and/or prevention of diseases induced by degradating abnormaly elastin, collagen fiber and/or proteoglycan, which are caused by the action of elastase in mammals, especially in human being. Examples of such diseases are pulmonary emphysema, interstitial pulmonary disease, diffuse panbronchialitis (DPB), atherosclerosis, rehumatoid arthritis and like.

On the other hand, derivatives of tetrazolylphenyl ester of pivalic acid of the general formura (1) of the present invention, and of the non-toxic salts and acid addition salts thereof, have an inhibitory effect on endotoxin induced lung injury.

Accordingly, the derivatives of the present invention are useful for treatment and prevention of respiratory distress syndrome (ARDS), diffuse panbronchialitis (DPB), interstitial pulmonary disease and like.

The inhibitory effects of the compounds of the present invention on elastase were confirmed by the following screening system.

INHIBITORY EFFECT ON ELASTASE (1) method of experiment

The test was carried out by a slight modification of the method of Costillo et al [Anal. Biochem., 99, 53 (1979)] using elastase from human neutrophil or human sputum. Namely, it is a spectrophotometric assay using the synthesized substrate, methoxysuccinyl-alanyl-alanyl- prolyl-valyl-p-nitroanilide(MeOSuc-Ala-Ala-Pro-Val-pNA, Cambridge research biochemical Co.) which has high specificity on neutrophil elastase.

20 μl of a test compound of various concentrations and 20 μl of enzyme solution (13 unit/ml) were added to 400 μl of 0.1M sodium phosphate buffer (pH 8.0). The mixture was incubated at 37° C. for 5 min, and then 20 μl of the substrate was added to the mixture in a final volume of 460 μl. The reaction was conducted by incubating thus obtained mixture at 37° C. for 20 min. The reaction was stopped by the addition of 300 μl of 20% acetic acid into the reaction mixture, and then p-nitroanilide released was measured by the spectrophotometrically at 405 nm.

Inhibition percents of the test compounds were calculated by the following equation:

Inhibition %=[1-(OD 405 nm value of the testing sample-background)/(OD 405 nm value of the control-background)]×100

(2) Results

The results are shown in Table 2.

TABLE 2

| Example No. | IC$_{50}$ (µM) | Example No. | IC$_{50}$ (µM) | Example No. | IC$_{50}$ (µM) |
|---|---|---|---|---|---|
| 3 | 2$^S$ | 38 | 0.8$^S$ | 75 | 0.08$^N$ |
| 6 | 4.4$^S$ | 39 | 0.08$^S$ | 76 | 0.18$^S$ |
| 7 | 0.54$^S$ | 40 | 0.25$^S$ | 77 | 0.15$^S$ |
| 8 | 0.23$^S$ | 41 | 0.065$^N$ | 78 | 0.091$^S$ |
| 9 | 0.17$^S$ | 42 | 0.019$^N$ | 79 | 0.14$^S$ |
| 10 | 0.8$^S$ | 42 | 0.022$^S$ | 81 | 0.059$^S$ |
| 11 | 0.85$^N$ | 43 | 0.13$^S$ | 82 | 0.092$^S$ |
| 12 | 0.51$^N$ | 44 | 0.085$^N$ | 83 | 0.084$^S$ |
| 13 | 0.072$^N$ | 45 | 0.13$^S$ | 84 | 0.72$^S$ |
| 14 | 0.076$^N$ | 46 | 0.089$^N$ | 85 | 0.077$^S$ |
| 15 | 0.094$^N$ | 47 | 0.14$^S$ | 86 | 0.08$^S$ |
| 16 | 0.03$^N$ | 48 | 0.7$^S$ | 87 | 0.058$^S$ |
| 16 | 0.15$^S$ | 49 | 0.7$^S$ | 88 | 0.65$^S$ |
| 17 | 0.1$^N$ | 50 | 1.7$^S$ | 89 | 0.17$^S$ |
| 18 | 0.017$^N$ | 51 | 0.038$^S$ | 90 | 0.11$^S$ |
| 18 | 0.16$^S$ | 52 | 0.35$^S$ | 91 | 0.58$^S$ |
| 19 | 0.042$^N$ | 53 | 0.11$^S$ | 92 | 1.6$^S$ |
| 19 | 0.51$^S$ | 54 | 0.056$^S$ | 93 | 0.52$^N$ |
| 20 | 0.09$^N$ | 55 | 1$^S$ | 94 | 0.096$^N$ |
| 21 | 0.062$^N$ | 56 | 0.42$^S$ | 95 | 0.25$^S$ |
| 22 | 4.3$^S$ | 57 | 0.42$^S$ | 96 | 0.14$^S$ |
| 23 | 0.022$^N$ | 58 | 0.029$^S$ | 97 | 0.15$^S$ |
| 24 | 0.1$^N$ | 59 | 0.04$^S$ | 98 | 0.15$^S$ |
| 25 | 0.28$^S$ | 60 | 0.058$^S$ | 99 | 0.34$^S$ |
| 26 | 0.27$^S$ | 61 | 0.03$^S$ | 100 | 0.25$^S$ |
| 27 | 0.09$^S$ | 62 | 0.079$^S$ | 101 | 0.38$^S$ |
| 28 | 0.22$^S$ | 63 | 0.3$^N$ | | |
| 29 | 0.1$^S$ | 67 | 0.13$^S$ | | |
| 30 | 0.38$^S$ | 68 | 0.2$^S$ | | |
| 31 | 0.1$^S$ | 69 | 0.82$^S$ | | |
| 32 | 0.38$^S$ | 70 | 1$^S$ | | |
| 35 | 0.014$^S$ | 71 | 0.26$^S$ | | |
| 36 | 0.8$^S$ | 72 | 0.5$^S$ | | |
| 37 | 0.18$^S$ | 74 | 0.098$^N$ | | |

N; human neutrophil elastase
S; human sputum elastase

INHIBITORY EFFECT ON PANCREATIC ELASTASE INDUCED ACUTE LUNG INJURY IN MICE (1) experiment ICR mice (25~30 g, ♂, n=7~8) were used.

The compound to be evaluated was suspended in 0.5% sodium carboxymethylcellulose-saline.

Oral administration of the test compound was given at 10 mg/Kg at 3. 5 hr before an intratacheal instillation of P. elastase (5 µg/site). After sodium pentobarbital anesthetized, sterile saline containing P. elastase was instilled intratracheally via ventral neck in the throat incisions using a 250 µl syringe attached to a 27-gauge needle.

The throat incisions were closed with surgical suture, and test compounds were administered with the same manner as described above at 4.5~5.0 hr after an intratracheal instillation of P. elastase.

At 20 hrs after an intratracheal instillation of P. elastase, animalz were euthanized by an i.p. pentobarbital overdose, each animal trachea was reexposed and the ventral nech region was small incised. A 10 cm length of small-diameter (O.D=0.5 mm) polyethylene catheter inserted and held in place using surgical suture. The lung were then lavaged with 500 µl sterile saline using a 1 ml syringe by gently expanding the lung and then withdrawing the saline.

The same operation was repeated 6 times, yielding in a final volume of 3 ml bronchoalveolar lavage (BAL) fluid from each animal.

The test compounds were evaluated as a inhabitory percent of hemorrhage and leukocyte number in the BAL fluid from each animal.

Operation for hemorrhage and leukocyte number assay;

Red blood cells were bursted with adding 50 µl KCN solution (0.33%) per 1 ml BAL fluid. The amount of blood in each BAL fluid sample was calculated from a hemoglobin standard curve.

BAL fluid was diluted to 100 fold with a balanced electrolyte solution and KCN solution (0.33%) was added to the diluted BAL fluid for lysis of contaminating red blood cells.

Leukocyte number was determined by the average of the three times count using a particle counter.

Inhibitory effects of the test compounds on hemorrhage and leukocyte infiltration were calculated from the following equation: Inhibitory percent=[1-(The average value of test compound group)/(The average value of the control group)]×100

The control animals were dosed orally with the same amount of vehicle before and after intratracheal instillation of P. elastase, and it were treated with the same manner as the test compound group.

(2) results

The results were estimated by the above method, the following compounds indicated inhibitory effects such as Table 3.

TABLE 3

| Example No. | Inhibitory percent of leukocyte infiltration (%) | Inhibitory percent of hemorrhage (%) |
|---|---|---|
| 7 | 26.1 | 23.6 |
| 16 | 49.0 | 44.0 |
| 19 | 14.1 | 76.8 |
| 35 | 45.1 | 71.5 |
| 95 | 30.2 | 15.2 |

INHIBITORY EFFECT ON ENDOTOXIN INDUCED ACUTE LUNG INJURY IN MICE (1) method of experiment ICR mice (25~30 g, ♂, n=7) were used.

The test compounds were suspended at 0.1% in 0.5% sodium carboxymethylcellulose-saline.

Oral administration of the test compounds were given at 10 mg/Kg at 1.5 hr before an intratracheal instillation of LPS (E.coli, 055:B5, Difico, 25 µg/site). After sodium pentobarbital anesthetized, LPS dissolved in sterile saline was instilled intratracheally via a ventral neck in the throat incisionusing with a 250 µl syringe attached to a 27-gauge needle.

The throat incisions were sutured with surgical threads, and PI-compound was administered with the same mannner as described above 4.5~5.0 hr after LPS instillation.

Up 19~20 hrs after LPS instillation, animals were euthanized by an i.p. pentobarbital overdose, each animal trachea was reexposed and the ventral neck region was small incised.

A 10 cm length of small-diameter (O.D=0.5 mm) polyethylene catheter inserted and held in place using surgical suture. The lung was then lavaged with a single 500 μl sterile saline using a 1 ml syringe by gently expanding the lung and then withdrawing the saline. The same operation was repeated 6 times, yielding a final volume of 3 ml bronchoalveolar lavage (BAL) fluid from each animal.

Evaluation of testing compounds were expressed as inhibitory percent of hemorrhage and leukocyte infiltration in the lung of each animals.

Estimation for hemorrhage:

Red blood cells were bursted with adding 50 μl KCN solution (0.33 %) per 1 ml of BAL fluid, and then the amount of blood in each BAL fluid samples were calculated from a hemoglobin standard curve.

Estimation of leukocyte infiltrations:

BAL fluid was diluted to 100 fold with a balanced electrolyte solution and KCN solution (0.33%) was added to the diluted BAL fluid for lysis of contaminating red blood cells.

Leukocyte number was determined from the average of the three times count using a particle counter.

The inhibitory effect of testing compounds were calculated from thefollowing equation:

Inhibitory percent=[1-(The average value of the test compound group)/(The average value of the control group)]×100

The control animals were dosed orally with the same amount of the vehicle before and after intratracheal instillation of LPS and were operated with the same manner as the animals tested with the test compounds.

(2) results

The results were estimated by the above mentioned method. The following compounds were shown a therapeutic effect such as Table 4.

TABLE 4

| Example No. | Inhibitory percent of leukocyte in filtration(%) | Inhibitory percent of hemorrhage (%) |
|---|---|---|
| 7 | 82.1 | 88.5 |
| 16 | 88.2 | 84.9 |
| 19 | 65.6 | 33.8 |
| 42 | 64.1 | 39.4 |
| 47 | 61.5 | 48.6 |
| 51 | 20.5 | 57.0 |
| 59 | 58.8 | 81.5 |
| 94 | 51.8 | 36.6 |
| 95 | 79.6 | 62.3 |

TOXICITY

It was confirmed that the compounds of the present invention had elastase inhibitory activity and a therapeutic effects on mice acute lung injury from the results of the above experiments.

CYTOTOXICITY TEST (1) Method of experiment

L1210 (lymphocytic leukemia, mouse) cells in a logarithmic growth phase were collected and washed twice with HBSS (Hanks' balanced salt solution). The L1210 cells were resuspended at $5.0 \times 10^4$ cells/ml in RPMI 1640 medium containing 10% heat-inactivated fetal bovine serum. The cell suspension was dispensed in 100 μl aliquots into 96 well multi-plate. Each of compounds to be tested was dissolved in dimethylsulfoxide at a concentration of 10 mM. The solutions were stepwise diluted with RPMI 1640 solution containing 10% heat-inactivated fetal bovine serum. Each of the diluted samples was dispensed in an amount of 10 μl well in the 96 well multi-plate containing L1210 cells and incubated for three days at 37° C. in humidified 5% $CO_2$-air mixture. To each of the wells, 10 μl of MTT (3-(4,5-dimethylthiazol-2-yl)-2,5-diphenyltetrazolium bromide)(5 mg/ml in phosphate buffer free of $Ca^{2+}$ and $Mg^{2+}$) was added. Cultivation was continued for additional five hours at 37° C. in humidified 5% $CO_2$-air mixture. To each of the wells, 100 μl of 20% SDS (sodium dodecyl sulfate) in 0.01N HCl was added to solubilize the MTT formazan.

Absorbance was measured at 630 nm as a reference wavelength and 570 nm as a measuring wavelength using Corona Electric MTP22 Microplate Photometer. The measurement was conducted three times for each of the samples to obtain an average value and a standard deviation. Survival rate was calculated by the following equation:

Survival rate (5)=[(absorbance of test sample)/(absobance of reference)]×100

(2) Results

The results are shown in Table 5.

TABLE 5

| | Survival rate (%) | | |
|---|---|---|---|
| | Final concentration of test compound | | |
| Example No. | 10 μM | 5 μM | 1 μM |
|---|---|---|---|
| 6 | 70.1 | 88.7 | 94.9 |
| 7 | 88.3 | 96.1 | 97.0 |
| 9 | 98.1 | 100.3 | 93.9 |
| 16 | 103.9 | 102.9 | 94.2 |
| 22 | 86.7 | 86.4 | 101.5 |
| 23 | 94.3 | 101.5 | 104.2 |
| 35 | 99.1 | 109.6 | 95.2 |
| 37 | 95.5 | 106.0 | 92.5 |
| 48 | 86.1 | 94.6 | 99.4 |
| 49 | 109.6 | 105.4 | 102.7 |
| 54 | 100.3 | 106.9 | 100.6 |
| 63 | 100.0 | 103.3 | 105.4 |
| 67 | 90.1 | 100.0 | 92.2 |
| 69 | 100.9 | 104.8 | 96.7 |
| 78 | 93.7 | 107.2 | 103.3 |
| 80 | 109.0 | 98.1 | 93.9 |
| 95 | 107.2 | 109.0 | 102.7 |

TOXICITY TEST OF A SINGLE ADMINISTRATION (1) The test compounds

The compounds of Examples 3, 7, 16, 19 and 35

(2) Method of experiment animals; ICR mice (25~30g, ♂, n=7) were used.

The test compounds were suspended in 1.2% sodium carboxylmethylcellulose-saline solution and were administered orally to mice. We observed symptom of each animals during 6 hr after the administration, furthermore, the observation of each animals was performed at more than once a day during 7 days.

(3) Results

The safety of the test compounds were confirmed from the results of the experiment which are shown in Table 6.

TABLE 6

| Testing Compound | dose (mg/kg) | Number of survival testing mice / Number of testing mice |
|---|---|---|
| Example 3 | 500 | 7 / 7 |
| Example 7 | 500 | 7 / 7 |
| Example 16 | 500 | 7 / 7 |

TABLE 6-continued

| Testing Compound | dose (mg/kg) | Number of survival testing mice / Number of testing mice |
|---|---|---|
| Example 19 | 500 | 6 / 7 |
| Example 35 | 500 | 7 / 7 |

APPLICATION

Accordingly, it was confirmed that the compounds of the present invention can be useful for the treatment and/or prevention of diseases induced by degradating abnormaly proteins such as elastin and the like, which are caused by the action of elastase in mamals, especially in human beings.

ADMINISTRATION

For the purpose mentioned above, the compounds of the present invention, described in the general formula (1) may normally be administered systemically or partially, usually by oral or parenteral administration.

The dose to be administered is determined depending upon age, body weight, symptom, the desired therapeutic effect, the route of administration, and the duration of the treatment etc. In the human adult, the doses per person for one time are generally between 10 mg and 500 mg, by oral administration up to several times per day, and between 1 mg and 200 mg, by parenteral administration up to several times per day.

As mentioned above, the dose to be used depend on various conditions. Therefore, there are cases in which dose lower than the ranges specified above and dose greater than the ranges specified above, may be used.

The compounds of the present invention can be shaped in any dosage form according to methods known pre se, such as tablets, film coated tablets, soft and hard capsules, powders, granules, sugar coated pills, suppositories, solutions, emulsions, suspensions, injections, eye drops, eye ointments and aerosols. Moreover, these pharmaceutical preparations may further comprise other substances having therapeutic activities.

What is claimed is:

1. A tetrazolylphenyl pivalate derivative represented by the following general formula or a pharmaceutically acceptable salt thereof:

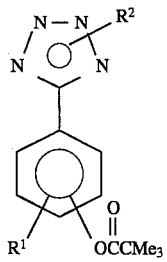

wherein $R^1$ represents a hydrogen atom, a lower alkyl group, a di-lower alkylamino group or a lower alkoxy group; $R^2$ represents (i) a hydrogen atom, (ii) a lower alkyl group, (iii) a group represented by the formula: —$(CH_2)_k$—$R^3$ (wherein k represents an integer ranging from 1 to 5 and $R^3$ represents an amino group, a carboxyl group, a hydroxyl group, a pyridyl group, a piperidinocarbonyl group, a phenylaminocarbonyl group, a guanidinobenzoyloxy group, a guanidinobenzoylamino group, a lower alkoxycarbonyl group, a di-lower alkylamino group, a tert-butoxycarbonylamino group, or an aralkyloxy group carrying a lower alkoxy group) or (iv) a group represented by the following general formula:

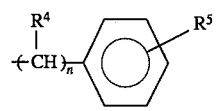

wherein n is an integer ranging from 0 to 4; $R^4$ represents a hydrogen atom, a phenyl group or a group: —CO—$R^{4\ 1}$ (wherein $R^{4\ 1}$ represents a hydroxyl group, a benzyloxy group or a glycine residue); $R^5$ represents a hydrogen atom, a hydroxyl, carboxyl, nitro, trihalomethyl, lower alkoxy, lower alkyl, lower alkanoyl, carboxy-lower alkoxy, carboxy-lower alkyl, amino-lower alkyl, amino-lower alkoxy, amino-lower alkanoylamino, tert-butoxycarbonyl-lower alkoxy, tert-butoxycarbonylamino-lower alkoxy, (tert-butoxycarbonyl) (lower alkyl)amino, lower alkoxycarbonyl, lower alkoxy group-carrying aralkyloxy, di-lower alkylamino-lower alkyl, di-lower alkylamino-lower alkoxy or lower alkanesulfonamido group, or a group: —CO—$R^{5\ 1}$ (wherein $R^{5\ 1}$ represents an amino acid residue, an amino acid benzyl ester residue, a benzyloxycarbonylamino-lower alkylamino group or an amino-monolower alkylamino group), or a group represented by the following general formula:

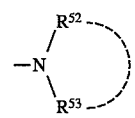

wherein $R^{5\ 2}$ and $R^{5\ 3}$ may be the same or different and each represents a hydrogen atom or a lower alkyl group or $R^{5\ 2}$ and $R^{5\ 3}$ may form a heterocyclic ring together with the nitrogen atom to which they are bonded.

2. The tetrazolylphenyl pivalate derivative of claim 1 wherein $R^1$ represents a hydrogen atom.

3. The tetrazolylphenyl pivalate derivative of claim 2 wherein $R^2$ represents a group represented by the formula: —$(CH_2)_k$—$R^3$ wherein k and $R^3$ are the same as defined in claim 1.

4. The tetrazolylphenyl pivalate derivative of claim 2 wherein $R^2$ represents a group represented by the following general formula:

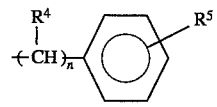

wherein n, $R^4$ and $R^5$ are the same as defined in claim 1.

5. The tetrazolylphenyl pivalate derivative of claim 3 wherein k is 1 and $R^3$ represents a pyridyl group.

6. The tetrazolylphenyl pivalate derivative of claim 4 wherein $R^4$ is a hydrogen atom, n is 1 and $R^5$ represents a lower alkyl group, —CO—$R^{5\ 1}$ or a group represented by the following general formula:

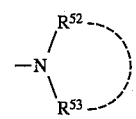

wherein $R^{5\ 1}$, $R^{5\ 2}$ and $R^{5\ 3}$ are the same as defined in claim 1.

7. The tetrazolylphenyl pivalate derivative of claim 6 wherein $R^{5\ 1}$ is an amino acid residue.

8. The tetrazolylphenyl pivalate derivative of claim 6 wherein $R^{52}$ and $R^{53}$ may be the same or different and each represents a hydrogen atom or a lower alkyl group.

9. The tetrazolylphenyl pivalate derivative of claim 8 wherein $R^{52}$ and $R^{53}$ may be the same or different and each represents a lower alkyl group.

10. The tetrazolylphenyl pivalate derivative of claim 6 wherein $R^5$ represents isopropyl group.

11. The tetrazolylphenyl pivalate derivative of claim 9 wherein $R^{52}$ and $R^{53}$ each represents methyl group.

12. The tetrazolylphenyl pivalate derivative of claim 7 wherein $R^{51}$ represents glutamic acid or valine residue.

13. The tetrazolylphenyl pivalate derivative of claim 1 wherein the derivative is a member selected from the group consisting of 4-[2-[4-(dimethylamino)benzyl]tetrazole-5-yl] phenyl pivalate, 4-[2-[4-(isopropylbenzyl)]tetrazol-5-yl] phenyl pivalate, 4-[2-(4-pyridylmethyl)tetrazole-5-yl]phenyl pivalate, N-[4-[5-(4-pivaloyloxyphenyl)tetrazol-2-ylmethyl]benzoyl]-L-glutamic acid and N-[4-[5-(4-pivaloyoxyphenyl)tetrazol- 2-ylmethyl]benzoyl]-L-valine.

14. The tetrazolylphenyl pivalate derivative of claim 1 wherein the lower alkyl group is a methyl, ethyl, propyl, isopropyl, butyl, isobutyl or tert-butyl group; the di-lower alkylamino group is a dimethylamino, diethylamino or dipropylamino group; the lower alkoxy group is a methoxy or ethoxy group; the lower alkoxy group-carrying aralkyloxy group is a methoxybenzyloxy group; the trihalomethyl group is a trifluoromethyl or trichloromethyl group; the lower alkanoyl group is a formyl, acetyl or propanoyl group; the carboxy-lower alkoxy group is a carboxymethoxy, 2-carboxyethoxy or 3-carboxypropoxy group; the carboxy-lower alkyl group is a carboxymethyl, 2-carboxyethyl or 3-carboxypropyl group; the amino-lower alkyl group is an aminomethyl, 2-aminoethyl, 3-aminopropyl or 4-aminobutyl group; the amino-lower alkoxy group is a 2-aminoethoxy, 3-aminopropoxy or 4-aminobutoxy group; the amino-lower alkanoylamino group is a 2-aminoacetylamino, 3-aminopropanoylamino or 4-aminobutanoylamino group; the tert-butoxycarbonyl-lower alkoxy group is a tert-butoxycarbonylmethoxy group; the tert-butoxycarbonylamino-lower alkoxy group is a 2-(tert-butoxycarbonylamino)ethoxy group; the (tert-butoxycarbonyl)(lower alkyl)amino group is a (tert-butoxycarbonyl)(methyl)amino, (tert-butoxycarbonyl)(ethyl)amino or (tert-butoxycarbonyl)(propyl)amino group; the lower alkoxycarbonyl group is a tert-butoxycarbonyl, butoxycarbonyl, propoxycarbonyl, ethoxycarbonyl or methoxycarbonyl group; the di-lower alkylamino-lower alkyl group is a dimethylaminomethyl, 2-dimethylaminoethyl, 3-dimethylaminopropyl, diethylaminomethyl, 2-diethylaminoethyl or 3-diethylaminopropyl group; the di-lower alkylamino-lower alkoxy group is a 2-dimethylaminoethoxy, 2-diethylaminoethoxy, 3-dimethylaminopropoxy or 3-diethylaminopropoxy group; the lower alkanesulfonamido group is a methanesulfonamido, ethanesulfonamido or propanesulfonamido group; the amino acid residue is a residue of glycine, alanine, phenylalanine, serine, threonine, cysteine, methionine, glutamic acid, lysine, proline, valine or ε-caproic acid; the amino acid benzyl ester residue is a residue of glycine benzyl ester, alanine benzyl ester, phenylalanine benzyl ester, serine benzyl ester, threonine benzyl ester, cysteine benzyl ester, methionine benzyl ester, glutamic acid benzyl ester, lysine benzyl ester, proline benzyl ester or valine benzyl ester; the benzyloxycarbonylamino-lower alkylamino group is a 2-(benzyloxycarbonylamino)ethylamino or 3-(benzyloxycarbonylamino)propylamino group; and the amino-mono-lower alkylamino group is a 2-aminoethylamino, 3-aminopropylamino or 4-aminobutylamino group.

15. The tetrazolylphenyl pivalate derivative of claim 1 wherein the pharmaceutically acceptable salt is a non-toxic and water-soluble acid-addition salt selected from the group consisting of hydrochlorides, hydrobromides, hydriodides, sulfates, phosphates, nitrates, acetates, lactates, tartrates, benzoates, citrates, methanesulfonates, ethanesulfonates, benzenesulfonates, toluenesulfonates, isethionates, glucuronates and gluconates.

16. The tetrazolylphenyl pivalate derivative of claim 1 wherein the pharmaceutically acceptable salt is a non-toxic and water-soluble salt selected from the group consisting of sodium and potassium salts; calcium and magnesium salts; ammonium salts; and salts with tetramethylammonium, triethylamine, methylamine, dimethylamine, cyclopentylamine, benzylamine, phenethylamine, pyridine, monoethanolamine, diethanolamine, tris(hydroxymethyl)aminomethane, lysine, alginine and N-methyl-D-glucamine.

17. A pharmaceutical composition comprising a pharmaceutically acceptable carrier and at least one member selected from the group consisting of tetrazolylphenyl pivalate derivatives represented by the following general formula and non-toxic or acid-addition salts thereof:

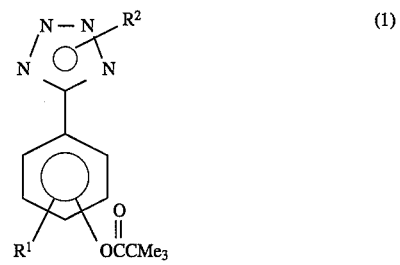

wherein all of the symbols representing substituents are the same as those defined in claim 1.

18. A method for preventing and treating emphysema comprising the steps of providing at least one compound selected from the group consisting of tetrazolylphenyl pivalate derivatives represented by the following general formula and non-toxic or acid-addition salts thereof:

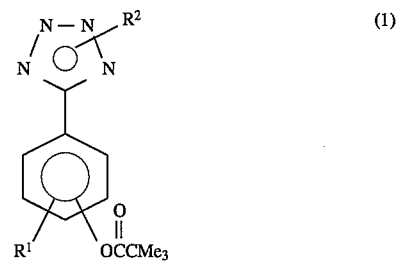

wherein all of the symbols representing substituents are the same as those defined in claim 1, and administering an effective amount of the compound to a mammal.

19. A method for preventing and treating endotoxin-induced lung disorders comprising the steps of providing at least one compound selected from the group consisting of tetrazolylphenyl pivalate derivatives represented by the following general formula and non-toxic or acid-addition salts thereof:

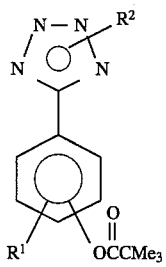

(1)

wherein all of the symbols representing substituents are the same as those defined in claim 1, and administering an effective amount of the compound to a mammal.

20. A method for preventing and treating endotoxin-induced lung disorders of claim 19 wherein the endotoxin-induced lung disorders are adult respiratory distress syndrome (ARDS cases), diffuse panlobular bronchitis or pneumonitis.

21. A method for the inhibition of elastase comprising the steps of providing at least one compound selected from the group consisting of tetrazolylphenyl pivalate derivatives represented by the following general formula and non-toxic or acid-addition salts thereof:

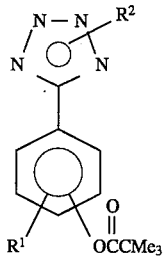

(1)

wherein all of the symbols representing substituents are the same as those defined in claim 1, and administering an effective amount of the compound to a mammal.

* * * * *